United States Patent
Monsigny et al.

(10) Patent No.: US 6,251,858 B1
(45) Date of Patent: Jun. 26, 2001

(54) DERIVATIVES OF OLIGOSIDES, THEIR PROCESS OF PREPARATION AND THEIR APPLICATIONS

(75) Inventors: Michel Monsigny, Saint-Cyr-en-Val; Annie-Claude Roche, Sandillon; Nadia Sdiqui; Roger Mayer, both of Orléans, all of (FR)

(73) Assignee: I.D.M. Immuno-Designed Molecules, Paris (FR)

( * ) Notice: Subject to any disclaimer, the term of this patent is extended or adjusted under 35 U.S.C. 154(b) by 0 days.

(21) Appl. No.: 08/591,481
(22) PCT Filed: Jun. 15, 1995
(86) PCT No.: PCT/FR95/00790
  § 371 Date: Feb. 21, 1996
  § 102(e) Date: Feb. 21, 1996
(87) PCT Pub. No.: WO96/00229
  PCT Pub. Date: Jan. 4, 1996

(30) Foreign Application Priority Data

Jun. 23, 1994 (FR) .................................................. 94 07738

(51) Int. Cl.$^7$ ..................................................... A61K 38/16
(52) U.S. Cl. ........................... 514/8; 514/414; 536/23.1; 536/123; 530/330; 530/322
(58) Field of Search .................... 530/330, 322; 514/8, 414; 536/23.1, 123

(56) References Cited

U.S. PATENT DOCUMENTS

| | | | |
|---|---|---|---|
| 4,478,744 | 10/1984 | Mezei et al. | 260/112.5 R |
| 5,028,594 | 7/1991 | Carson | 514/23 |

FOREIGN PATENT DOCUMENTS

| | | |
|---|---|---|
| 2277823 | 2/1976 | (FR) . |
| WO 88/00592 | 1/1988 | (WO) . |
| WO 93/04701 | 3/1993 | (WO) . |
| WO 94/03184 | 2/1994 | (WO) . |

OTHER PUBLICATIONS

Reutter et al., *Z. Lebensm.—Unters. Forsch*, 188(1), 28–35. (abstract), 1989.*

E. Bonfils et al., "Drug targeting: synthesis and endocytosis of oligonucleotide–neoglycoprotein conjugates", *Nucleic Acids Research*, vol. 20, No. 17, Sep. 11, 1992, pp. 4621–4629.

* cited by examiner

*Primary Examiner*—Dwayne C. Jones
*Assistant Examiner*—C. Delacroix-Muirheid
(74) *Attorney, Agent, or Firm*—Young & Thompson

(57) ABSTRACT

The invention relates to compounds comprising one or several oligosides, each of said oligosides being fixed in a covalent manner on one or many molecules, matrixs or particles, specifically one, two or three, via an intermediary molecule possessing a nitrogen atom carried by a carbon in α of a C=O group and one or many functional groups, specifically one, two or three, the covalent bond between said intermediary molecule and the oligoside being done by the intermediary of said nitrogen atom, and the covalent bond between said intermediary molecule and said molecule, said matrix, said particle, or said molecules, said matrixs, said particles being done by the intermediary of the said functional groups of said intermediary molecule and appropriate functional groups to the molecule(s), the matrix (ces) or the particle(s).

17 Claims, 2 Drawing Sheets

DERIVATIVES OF OLIGOSIDES, THEIR PROCESS OF PREPARATION AND THEIR APPLICATIONS

This application is a 371 of PCT/FR95/00790 filed Jun. 15, 1995.

BACKGROUND OF THE INVENTION

1. Field of the Invention

The invention relates to oligoside derivatives, their process of preparation, and their applications.

2. Description of the Related Art

Natural oligosides are able to be prepared in free form from various physiologic liquids such as milk, or extracts from natural or transformed products (honey, beer, etc.). Natural oligosides are also able to be obtained by cutting a glycoside bond from one of the sugar moieties of glycoconjugates (glycolipids, glycoproteins, polyosides, proteoglycans, etc.), by hydrolysis with the aid of enzymes or by chemical catalysis from said glycoconjugates.

The natural oligosides are able to be used as substrates, as inhibitors, as recognition signals, etc. In the majority of cases, it is advisable to fix the oligoside on a molecule, matrix or particle, which can be chosen from:

a matrix as a support for affinity chromatography;

a bead of gold or latex, for histology and cytology;

a protein for visualilzation, purification, etc., in particular
1) specific receptors of osides, receptors which are called lectins, adhesins, agglutinins, etc., or 2) proteins with or without enzymatic activity, which have an affinity for the osides, in particular the glycosyltransferases, exoglycosidases or endoglycosidases a lipid for the characterization of the preceding receptors;

oligonucleotides for selectively increasing their capture by targeted cells;

a protein or polymers for the targeting of drugs, oligonucleotides or genes, or for obtaining intramolecular inhibitors.

The synthesis of derivatives of oligosides able to be linked by covalent means to a protein, a matrix, an oligonucleotide, or by general means to an organic molecule or a particle, in all cases preserving the integrity of the structure and functions of each of its sugar components—which is necessary for preserving the functional capacity of the oligoside can be obtained essentially in two ways: the total synthesis de novo and the intermediary transformation into glycosylamine. A third way which leads to an equally useful derivative but which destroys the terminal reductorose is amination in a reducing medium.

Concerning total synthesis, this requires a selective protection of the hydroxyls non-engaged in a glycoside bond, steps of condensation, steps of selective deprotection, and a step of final deprotection. Even if over the last decades the yields of some of these steps were able to be improved, this is a long process and the overall yield remains modest, and this all the more as the oligoside to be synthesized is more complex.

The yields for each step are between 20 and 95% according to the steps considered.

For example, the synthesis of a para-nitrophenyl derivative of a pentasaccharide such as the determinant of Lewis x:

requires in total several tens of steps. Each step has a yield of between 50 and 95%, more generally 80%. In total the yield of the product sought is of some %.

The elevated number of steps arises from the fact that the alcohol functions of each ose must be protected in a different manner depending on whether the hydroxyl under consideration will or will not be implicated in a condensation reaction.

A sugar such as GlcNAc which will be substituted 2 times will receive momentarily 3 different substitutes in order to permit a selective substitution on the hydroxyl 3 by galactose, on the hydroxyl 4 by fucose, the hydroxyl 6 remaining protected until the final deprotection.

For each step of condensation, the yield is affected by the fact that the product formed is in general a mixture of the two ($\alpha$ and $\beta$) anomeric forms.

Moreover, it is necessary to point out that the intermediary products have to be purified, either by crystallization, or by chromatography, which contributes significantly to the total duration of the synthesis. Finally, it should be noted that the yields may be very weak for certain steps because of steric hindrance, which is specifically the case at the level of the branches: 2 sugars substituting a single monosaccharide.

All in all, this global synthesis is very costly and takes a long time.

In the case of the formation of a glycosylamine followed by acylation, this way depends on a reaction described at the end of the last century: an oside possessing a reducing sugar, incubated in the presence of an elevated concentration of ammoniac, of an ammonium salt or an aromatic amine, is transformed in a reversible manner into glycosylamine.

For example, the lactose gives a lactosylamine, with ammoniac:

or with the aniline:

This reaction is however reversible, which is to say the isolated product, dissolved in a buffer, becomes hydrolyzed leading to give back the original products.

The glycosylamine may however be stabilized by acylation, for example by selective N-acetylation:

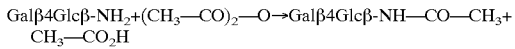

On these bases, it has recently been proposed to substitute the amine of oligosylamines by an organic compound possessing a finctional reactive group. Manger et al., 1992, Biochemistry 31, 10724 and 31, 10733.

This route comprises the following steps:

1) incubation of the oside possessing a terminal reducing sugar in the presence of a highly concentrated ammonium salt.

For example,

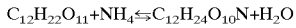

2) Purification of the glycosylamine by chromatography on a column to eliminate the ammonium salt excess.

3) Substitution of the amine of the glycosylamine by reaction with an activated derivative of monochloroacetic acid, in alkaline medium.

For example,

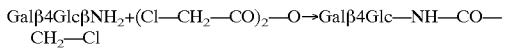

4) Transformation of the chloroacetyl residues into glycyl residue.

The chloroacetylglycosylamide is incubated in the presence of a highly concentrated ammonium salt, which allows the introduction of an amine function. For example:

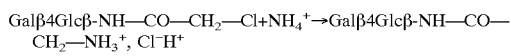

5) Purification of glycyl-glycosylamide by chromatography on column to eliminate the ammonium salts.

6) Condensation of the glycyl-glycosylamide and of a compound able to selectively react with an amine group of the glycyl residue.

For example:

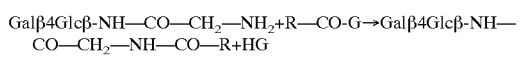

in which G is an activator of the carboxylic function.

This route in 6 steps implies two steps of intermediary purification and the use of a toxic product: an activated derivative of chloroacetic acid.

The yield of each step is variable and ranges between 50 and 95%; the global yield is less than approximately 60%.

Another pathway has also been suggested, but it requires the transformation of the reducing sugar into polyol; this route was proposed in 1974 by Gray (Arch. Biochem. Biophys., 163, 426–428).

The oligoside is condensed with a compound comprising one (or many) amine function(s) in the presence of sodium cyanoborohydride in alkaline medium; the imine formed between the reducing sugar and the amine is reduced by the sodium cyanoborohydride into a secondary amine.

For example:

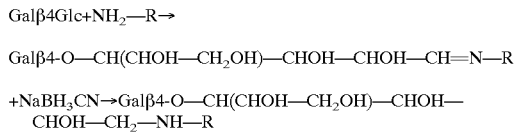

The yield of this reaction varies according to the size of the partners and is usually between 5 and 70%.

There is a destruction of the reducing sugar, which is not desirable.

French patent number 2 227 823 concerns the N-osides of L pyrrolidone-2-carboxylic-5 acid, derivatives of said acid and their procedure of preparation, consisting of condensing the L pyrrolidone-2-carboxylic-5 acid and/or the L-glutamic acid and/or a salt of these acids with an ose or an oside, with reducing or non-reducing properties.

Following the examples, the reducing sugars are all monosaccharides (ketoses or aldoses), while the non-reducing sugars are, for example, saccharose; taking into consideration the reaction conditions, the saccharose becomes hydrolyzed into glucose and fructose.

It should also be noted that, in the procedure of the said French patent number 2 227 823, condensation takes place preferably in an aqueous medium, at a temperature between 50° C. and 150° C., preferably at approximately 105° C.

These operating conditions require working with very concentrated solutions of sugar and acid which are inapplicable in the preparation of oligosides; the solubility of oligosides decreases rapidly while the number of sugars increases.

Furthermore, the condensation reaction between the sugar and the acid being a thermic dehydration, it is inapplicable to the preparation of oligosides because of the fragility of the oside linkages, which are easily hydrolyzed in hot conditions (see for example the case of saccharose).

Thermic condensation presents, moreover, the drawback of giving colored products, which are the evidence of degradation reactions and require a further step of purification.

The procedure thus does not allow obtaining anything but derivatives of monosaccharides and is not adapted to the production of derivatives of oligosides.

SUMMARY OF THE INVENTION

One of the aspects of the invention is to propose new derivatives of glycosylamine in which the oligosides are fixed on at least one molecule, matrix or particle.

One of the aspects of the invention is to propose derivatives of glycosylamine, stable in aqueous medium, able to be fixed on at least one molecule, matrix or particle.

Another object of the present invention is to furnish a process for the preparation of oligosides fixed on at least one molecule, one matrix, or one particle, easy to carry out, presenting a reduced number of steps and allowing to obtain a yield which can, in practice, reach substantially 100%.

Another aspect of the invention is the ability to fix oligosides covalently on at least one molecule, matrix, or particle, always preserving the functional capacity of the oligosides.

The invention relates to new compounds comprising one or several oligosides, each of said oligosides being fixed covalently on one or several molecules, matrices or particles, specifically on one, two or three, via an intermediary molecule possessing a nitrogen atom carried by an α carbon of a C=O group and one or several functional groups, in particular one, two, or three, the covalent bond between said intermediary molecule and the oligoside taking place by the intermediary of the aforementioned nitrogen, and the covalent bond between said intermediary molecule and the aforementioned molecule, the aforementioned matrix, the aforementioned particle, or the aforementioned molecules, the aforementioned matrices, the aforementioned particles taking place by the intermediary of the aforementioned functional group or groups of the said intermediary molecule and the appropriate functional groups on the molecule(s), matrix(ces), or particle(s).

The term oligosides corresponds to the presence of at least two, advantageously to the presence of more than two sugars, and advantageously to at least 4.

The oligosides entering into the constitution of the compounds of the invention are such that before the linkage with the intermediary molecule, they present a terminal reducing sugar. Because of this, the covalent linkage between the said intermediary molecule and the oligoside takes place by the intermediary of the nitrogen atom of the intermediary molecule and of the anomeric carbon of the terminal reducing sugar, it is to say the carbon in position 1 of the terminal reducing sugar of the aldose series, or the carbon in position 2 of the terminal reducing sugar of the cetose series.

The invention is of compounds of the general formula (I)

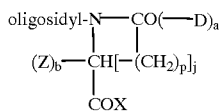
(I)

in which:
a=0 or 1,
j=0 or 1,
b=0 or 1,
p=2 to 4, in particular 2,
provided that
   a=b=0, when j=1, which leads to the presence of a cyclic molecule,
   or a=b=1, when j=0 which implies the absence of the $(CH_2)_p$ group,
D represents a residue of an organic acid of the formula $DCO_2H$, in particular H or an alkyl chain of 1 to 10 carbon atoms, in particular $CH_3$,
Z represents
   B, B being H, an alkyl of 1 to 10 carbon atoms or a side chain of an α amino acid, natural or synthetic, such as $CH(CH_3)_2$, $CH_2OH$, $CH_3$, and preferably H, or
   B'-P', B' being an alkylene chain of 1 to 10 carbon atoms or a side chain on an α amino acid, natural or synthetic, the said chains containing a group derived from a functional group able to be activated, such as carboxylic, thiol, hydroxyl, or amine, free or protected, preferably protected, P' having the significations indicated hereafter,
X represents:

• the group $[NH\text{---}(A_i)\text{---}CO]_{\overline{m}}\text{---}Q$,
   with $(P'')_k$

• or the group $[NH\text{---}(A_i)\text{---}CO]_{\overline{m}}\text{---}P$,
   with $(P'')_k$

• or the group $[NH\text{---}(A_i)\text{---}CO]_{\overline{m}}\text{---}R\text{---}P$,
   with $(P'')_k$ m being an integer from 0 to 10, preferably from 0 to 5 and advantageously 1 or 2, k=0 or 1
Q representing OH, $OCH_3$, $OCH_2\text{---}C_6H_5$, $O\text{---}C_6H_5$, $O\text{---}C_6F_5$,

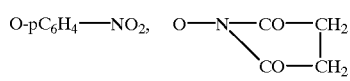

R representing a group possessing an alcohol, phenol, thiol, or amine function,
P being such as is defined hereafter,
$A_i$ representing an organic radical such as an alkylene chain of 1 to 10 carbon atoms, in particular $(CH_2)_n\text{---}W\text{---}(CH_2)_{n'}$, n+n' representing an integer from 0 to 10, W representing CHY, Y being H, an alkyl from 1 to 6 linear or branched carbon atoms, an α amino acid residue, natural or synthetic, or W representing an aromatic compound, in particular phenylgroup,
P, P' and P" are identical or different and represent:

a matrice as a support for the affinity chromatography;
a bead of gold, of latex, for histology and cytology;
a protein for the visualization, purification, etc., in particular 1) specific receptors of osides, receptors which are called lectins, adhesins, agglutinins, etc., or 2) proteins with or without enzymatic activity, which have an affinity for the osides, in particular the glycosyltransferases, such as sialyltransferase, sulfotransferases, phosphotransferases, exoglycosidases, or endoglycosidases;
a lipid for the characterization of the preceding receptors;
oligonucleotides to selectively increase their capture by target cells;
a protein or polymers for the targeting of drugs, oligonucleotides or genes;
P, P' and P" possessing at least one function allowing a condensation reaction by reaction with an oligopeptide, for example
   an amine function ($\text{---}NH_2$) allowing the formation of an amide with an active ester, an amidine with an imidate, a thiourea with an isothiocyanate,
   a thiol function ($\text{---}SH$) allowing the formation of a disulfide bridge with an oligopeptide containing a thiol, a thioether with an oligopeptide containing a maleimide group, or halogeno-alkyle, or a halogeno-alkanoyle,
   a phenol ($\text{---}C_6H_4OH$) allowing the formation of an azoic with an oligopeptide containing a diazoide,
provided that if Z represents B'---P', and/or X comprises P and/or P" in the formula.

In formula I and in those which follow, the oligosidyl group derives from an oligoside whose terminal sugar is reductive.

It is recognized that in the definition of compounds of the general formula (I) indicated here above, the above mentioned intermediary molecule includes in its structure the following chemical entity:

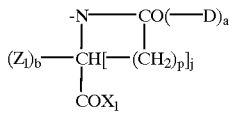

in which D, a, b, j and p are such as defined above, $Z_1$ and $X_1$ comprise one or many functional groups able to form at least one bond with one (or many) molecule(s), or one (or several) matrix (ces), hereabove mentioned, and $Z_1$ and $X_1$ being more precisely defined in that which follows (see products of formula Ia defined hereinafter).

In the definitions above, the amino acids implied have configuration L or D, and preferably L.

The compounds of the invention are thus constituted of one or many oligosides (identical or possibly different), each of these oligosides being attached:
   to a molecule, matrix or particle, by the intermediary of either a functional group X, or a functional group Z,
   or to two molecules, matrices or particles, by the respective functional groups X and Z, or by the intermediary of two functional groups X, or to three molecules, matrices or particles, by the intermediary of functional groups X and Z.

It should be noted that the general formula (I) represents only the following possibilities:
   a single oligoside fixed to a molecule, matrice, or particle, P, a single oligoside fixed to a molecule, matrice, or particle, P', a single oligoside fixed to a molecule, matrice, or particle, P", a single oligoside fixed to two molecules, matrices, or particles, P and P' respectively, or P' and P", or P and P', a single oligoside fixed to three molecules, matrices, or particles, P, P', and P".

The reason for such representation is to not complicate the comprehension of the general formula (I). But one can envision the possibility of many oligosides (identical or possibly different) being fixed either on a molecule, matrix, or particle, P, or on a molecule, matrix or particle, P', or on a molecule, matrix or particle, P", or that many oligosides (identical or possibly different) could be fixed on two molecules, matrices or particles, P and P', or P and P", or P' and P", or that many oligosides (identical or possibly different) could be fixed on three molecules, matrices or particles, P, P' and P".

As an example of B' one can mention:

—CH$_2$—S—

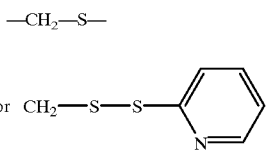

or

—(CH$_2$)$_3$—NH— or

—(CH$_2$)$_4$—NH—

As an example of P, or P' or P", on can mention polylysine, in particular gluconoylated polylysine.

According to an advantageous mode of embodiment of the invention, one or many oligosides are linked to the same molecule, matrice or particle, P, constituting compounds able to be represented by the general formula (II)

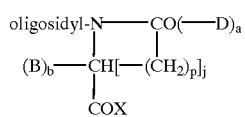

(II)

in which:

a=0 or 1, j=0 or 1, b=0 or 1, p=2 to 4, in particular 2, provided that a=b=0, when j=1, which leads to the presence of a cyclic molecule, or a=b=1, when j=0 which implies the absence of the (CH$_2$)$_p$ group, D represents a residue of an organic acid of the formula DCO$_2$H, in particular H or an alkyl chain of 1 to 10 carbon atoms, in particular CH$_3$, B represents H, an alkyl of 1 to 10 carbon atoms, or a side chain of an α amino acid such as CH(CH$_3$)$_2$, CH$_2$OH, CH$_3$, and preferably H, X represents:

either the group [NH—(A$_i$)—CO]$_m$—P, or the group [NH—(A$_i$)—CO]$_m$—R—P m being an integer from 0 to 10, preferably from 0 to 5 and advantageously 1 or 2, R and P being as defined hereinafter, A$_i$ represents an organic radical such as an alkylene chain of 1 to 10 carbon atoms, in particular (CH$_2$)$_n$—W—(CH$_2$)$_{n'}$, n+n' representing an integer from 0 to 10, W representing CHY, Y being H, an alkyl from 1 to 6 linear or branched carbon atoms, an α amino acid residue, natural or synthetic, or W representing an aromatic compound, in particular phenyl, R represents a group possessing an alcohol, phenol, thiol, or amine function, P represents:

a matrice as a support for affinity chromatography;

a bead of gold, of latex, for histology and cytology;

a protein for the visualization, purification, etc., specific receptors of osides, receptors which are called lectins, adhesins, agglutinins, etc., a lipid for the characterization of the preceding receptors;

oligonucleotides to selectively increase their capture by target cells;

a protein or polymers for the targeting of medicines, oligonucleotides or genes.

An advantageous class of compounds according to the invention fulfills the general formula (III)

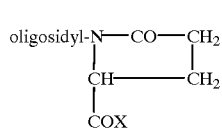

(III)

in which X represents [NH—(A$_i$)—CO]$_m$—P or [NH—(A$_i$)—CO]$_m$—R—P, A$_i$, m, P and R having the significations indicated above.

An advantageous class of compounds according to the invention fulfills the formula (III):

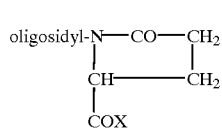

(III)

in which X represents:

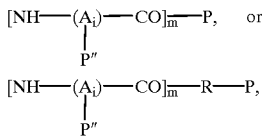

A$_i$, m, P, R and P" having the significations indicated above.

Another advantageous class of compounds according to the invention has as a general formula (IV):

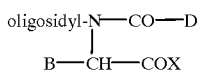
(IV)

in which D and B have the significations indicated above, and X represents $[NH-(A_i)-CO]_m-P$ or $[NH-(A_i)-CO]_m-R-P$, $A_i$, m, R and P having the significations indicated above.

Another advantageous class of compounds according to the invention fulfills the formula (IV):

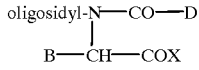
(IV)

in which D and B have the significations indicated above, and X represents:

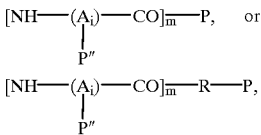

$A_i$, m, R, P and P" having the significations indicated above.

Another advantageous class of compounds according to the invention has as a general formula (V):

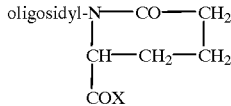
(V)

in which X represents $[NH-(A_i)-CO]_m-P$ or $[NH-(A_i)-CO]_m-R-P$, P, $A_i$, m and R having the significations indicated above.

The invention also relates to new products, able in particular to serve as intermediary products for the preparation of compounds of the invention, said products comprising an oligoside linked to a molecule possessing a nitrogen atom, carried by an a carbon of α C=O group, and at least one functional group, in particular one, two or three functional groups, the covalent link between the oligoside and the molecule being made by the intermediary of the said nitrogen atom.

The products of the invention advantageously fulfill the general formula (Ia):

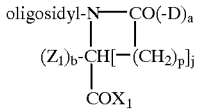
(Ia)

in which:
 a=0 or 1,
 j=0 or 1,
 b=0 or 1,
 p=2 to 4, in particular 2, provided that
 a=b=0, when j=1, which leads to the presence of a cyclic molecule,
 or a=b=1, when j=0 which implies the absence of the $(CH_2)_p$ group,
D represents a residue of an organic acid of the formula $DCO_2H$, in particular H or an alkyl chain of 1 to 10 carbon atoms, in particular $CH_3$,
$Z_1$ represents
 B, B being chosen from among: H, an alkyl chain of 1 to 10 carbon atoms, or a lateral chain of an α amino acid such as $CH(CH_3)_2$, $CH_2OH$, $CH_3$, and preferably H, or
 B', B' being chosen from among: an alkylene chain of 1 to 10 carbon atoms, or a lateral chain of an α amino acid, said chains containing a functional group such as carboxylic, SH, OH or amine, free or protected,
$X_1$ represents
 the group $[NH-(A_i)-CO]_m-R$,
 or $[NH-(A_i)-CO]_m-Q$
R representing a group possessing an alcohol, phenol, thiol, or amine function,
Q representing OH, $OCH_3$, $OCH_2-C_6H_5$, $O-C_6H_5$, $O-C_6F_5$,

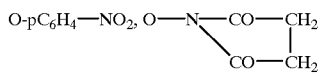

m being an integer from 0 to 10, preferably from 0 to 5 and advantageously 1 or 2,
$A_1$ represents an organic radical such as an alkylene chain from 1 to 10 carbon atoms, in particular $(CH_2)_n-W-(CH_2)_{n'}$, n+n' representing an integer from 1 to 10, W representing CHY, Y being H, an alkyl from 1 to 6 linear or branched carbon atoms, an α amino acid residue, natural or synthetic, or W representing an aromatic compound, in particular phenyl.

These groups are derivatives of acylated glycosylamine.

The derivatives of acylated glycosylamine are stable, in an aqueous medium in a large range of pH on each side of neutrality. This signifies that a hydrolysis of less than 1% at pH 5–8 is produced, over 24 h, whatever the temperature may be between 0 and 95° C.

The said products of formula (Ia) are able to be utilized as such.

The said products of formula (Ia) are also able to be utilized in order to prepare the compounds of the invention of formula I.

An advantageous class of products according to the invention fulfills the general formula (IIa):

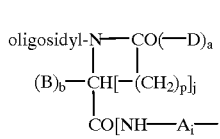
(IIa)

in which:
 a=0 or 1,
 j=0 or 1,
 b=0 or 1,
 p=2 to 4, in particular 2,
provided that a=b=0, when j=1, which leads to the presence of a cyclic molecule, or a=b=1, when j=0 which implies the absence of the $(CH_2)_p$ group, D represents a residue of an organic acid of the formula $DCO_2H$, in particular H or an alkyl chain of 1 to 10 carbon atoms, in particular $CH_3$, B represents H, an alkyl chain of 1 to 10 carbon atoms, or a side chain of an α amino acid such as $CH(CH_3)_2$, $CH_2OH$, $CH_3$, and preferably H, m being an integer from 1 to 10, preferably from 0 to 5 and advantageously 1 or 2, $A_1$ represents an organic radical such as an alkylene chain from 1 to 10 carbon atoms, in particular $(CH_2)_n$—W—$(CH_2)_{n'}$, n+n' representing an integer from 1 to 10, W representing CHY, Y being H, an alkyl from 1 to 6 linear or ramified carbon atoms, an α amino acid residue, natural or synthetic, or W representing an aromatic compound, in particular phenyl, R represents a compound possessing an alcohol, phenol, thiol or amine function.

The said products of formula (IIa) are able to be used to prepare the compounds of formula (II).

Another advantageous class of products according to the invention fulfills the general formula (IIIa):

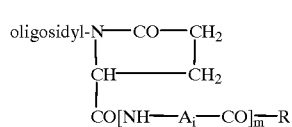

(IIIa)

in which $A_1$, m and R have the significations indicated above.

The said products of formula (IIIa) are able to be utilized to prepare the compounds of formula (III).

Another advantageously class of products according to the invention fulfills the general formula (IVa):

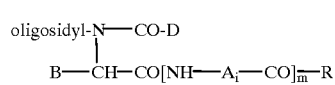

(IVa)

in which D, B, m, $A_1$ and R have the significations indicated above.

The said products of formula (IVa) are able to be used to prepare the compounds of formula (IV).

Another advantageously class of products according to the invention fulfills the general formula (Va):

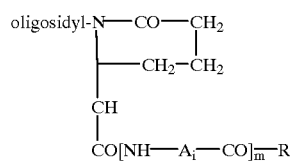

(Va)

in which $A_1$, m and R have the significations indicated above.

The said products of formula (Va) are able to be used to prepare the compounds of formula (V).

The product of formula (VI):

(VI)

in which B, $A_1$, m and R have the significations indicated above, are intermediary products obtained during the preparation of the products defined above and are new.

The products of formula (VII)

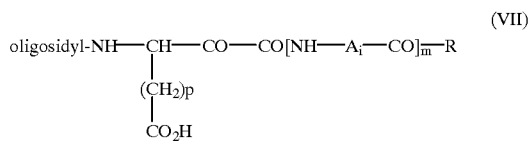

(VII)

in which p, $A_1$, R and m have the significations indicated above, are intermediary products obtained during the preparation of the products defined above and are new.

In all of the compounds or products of the invention, R can represent the following radicals:

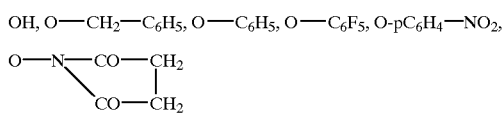

—NH-$pC_6H_4$—N=C=S and its precursors:
—NH-$pC_6H_4$—$NO_2$
—NH-$pC_6H_4$—$NH_2$
—NH—$CH_2$—$(CH_2)_m$—C(=$NH_2^+$)$OCH_3$
—NH—$CH_2$—$(CH_2)_m$—CN
—NH—$CH_2$—$(CH_2)_m$—$CH_2$—NH—CO—$CH_2$—$(CH_2)_m$—C(=$NH_2^+$)$OCH_3$
—NH—$CH_2$—$(CH_2)_m$—$CH_2$—NH—CO—$CH_2$—$(CH_2)_m$—CN these compounds allowing for the addition on one of the amino compounds.

R can also represent

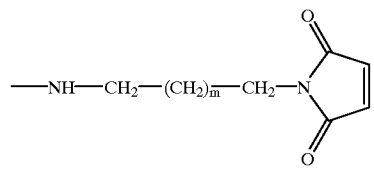

derivative of maleimide

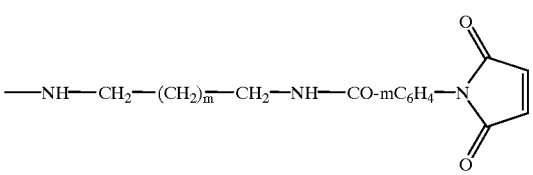

derivative of m-maleimidyl benzoyl

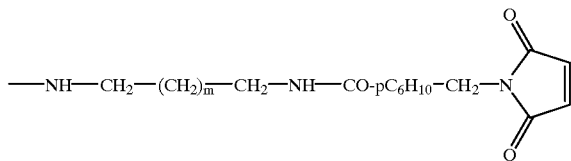

derivative of N-methylmaleimidyl p-cyclohexylcarboxy-
—NH—CH$_2$—(CH$_2$)$_m$—CH$_2$—NH—CO—CH$_2$-T
T=Br, I, Cl
derivative of halogenoacetyl
—NH—CH$_2$—CH$_2$—NH—CO—CH$_2$—(CH$_2$)$_m$—S—S-Pyr
derivative of dithiopyridine
N.B.: -Pyr: -2-pyridine
—NH—CH$_2$—(CH$_2$)$_m$—CH$_2$—S—S-Pyr
derivative of dithiopyridine
these compounds allowing the addition on a thiol.

R can also represent:

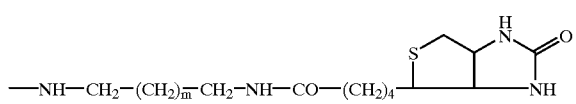

derivative of biotin
this compound including a biotin residue which allows the formation of a complex with avidine or streptavidine.

R can also represent:

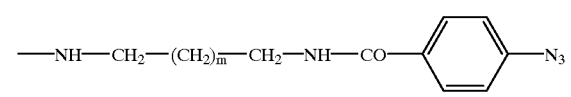

derivative of 4-azidobenzoyl

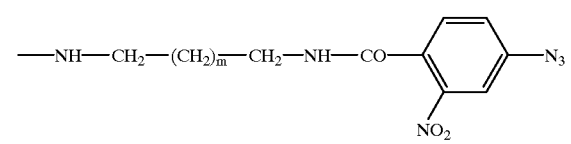

derivative of 4-azido 2-nitrobenzoyl

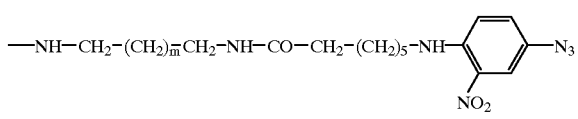

derivative of 4-azido 2-nitroanilide

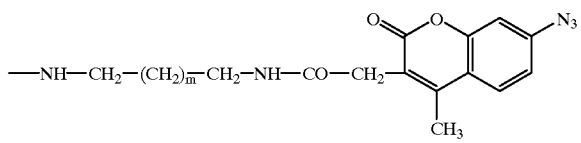

derivative of 7-azido 4-methylcoumarine 3-acetyl

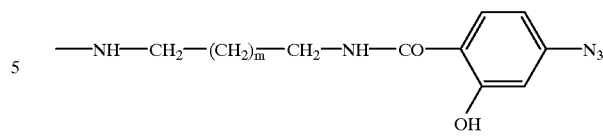

derivative of 4-azidosalicyclique or of 4-azido 2-hydroxybenzoyle these compounds allowing the covalent fixation on a receptor, an enzyme, an antibody, specific to the glucidic part by photonic activation.

R can also represent:
—NH—(CH$_2$)$_m$-pC$_6$H$_4$OH
—NH—CH$_2$—(CH$_2$)$_m$—CH$_2$—NH—CO—(CH$_2$)$_m$-pC$_6$H$_4$OH these compounds allowing the fixation of one or two iodine atoms, specifically of a radioactive iodine atom.

R can also represent:

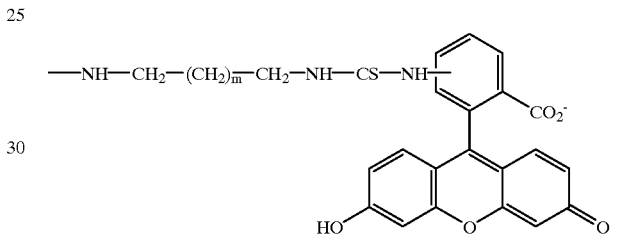

derivative of fluoresceine

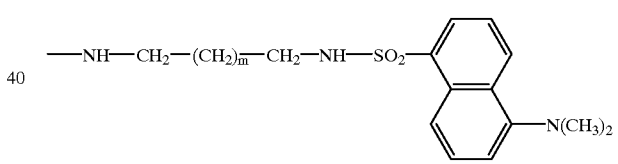

derivative of dansyl

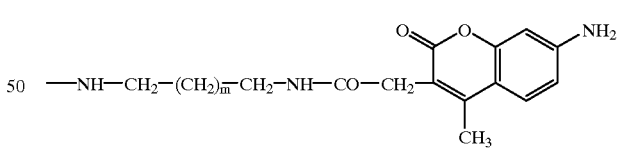

derivative of 7-amino 4-methylcoumarin 3-acetyl

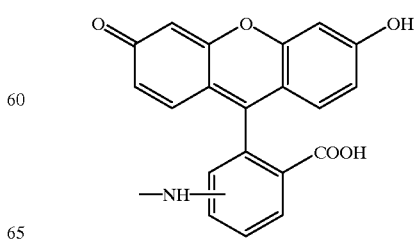

derivative of amino-fluoresceine

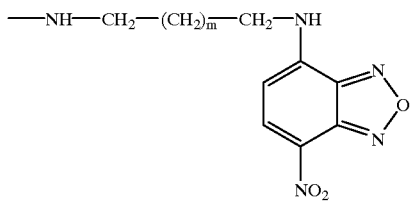

derivative of nitrobenzoxadiazole these fluorescent compounds allowing visualizing the position of the oligosidylpeptide in a cell, a tissue, an organ, on a gel or an electrophoresis band, etc.

In the compounds of the invention, P can represent an oligopeptide, or a polypeptide, in particular gluconoylated polylysine, and P' or P'' can represent an oligonucleotide, or R can represent fluoresceine or one of its derivatives or another fluorescent derivative, and P' or P'' can represent an oligonucleotide. P can also represent a therapeutic agent or any molecule of interest.

In the compounds and products of the invention, the oligosidic residue comprises from 2 to 50 oses and in particular is chosen from

| | |
|---|---|
| lacto-N-tetraose | Galβ 3 GlcNAcβ 3 Galβ 4 Glc |
| neolacto-N-tetraose | Galβ 4 GlcNAcβ 3 Galβ 4 Glc |
| Group H | Fuc α 2 Galβ 3 Galβ 4 Glc |
| Lewis[a] | Galβ 3 GlcNAcβ 3 Galβ 4 Glc |
| | Fuc α 4-↑ |
| Lewis[x] | Galβ 4 GlcNAcβ 3 Galβ 4 Glc |
| | Fuc α 3-↑ |
| Lewis[b] | Fuc α 2 Galβ 3 GlcNAc β 3 Galβ 4 Glc |
| | Fuc α 4-↑ |
| Lewis[y] | Fuc α 2 Galβ 4 GlcNAcβ 3 Galβ 4 Glc |
| | Fuc α 3-↑ |
| Disialolacto-N-tetraose | Neu 5Acα 3 Gal β 3 GlcNAc β 3 Gal β 4 Glc |
| | Neu 5Acα 6-↑ |
| Three antenna complex type | |

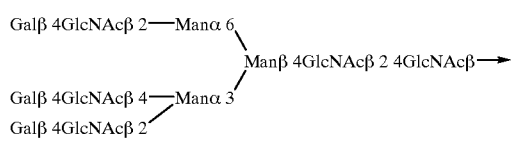

| | |
|---|---|
| Silaylactose 3 | Neu 5Ac α 3 Gal 4 Glc |
| Sialylactose 6 | Neu 5Ac α 6 Gal β 4 Glc |
| Disialylactose 3 | Neu 5Ac α 8 Neu 5Ac α 3 Gal β 4 Glc | simple or complex osides recognized by the lectin membranes, and chosen from:

a. Asialo-oligoside of type lactosamine triantenna: receptor of asialoglycoprotein Galβ 4GlcNAcβ 2—Manα 6
　　　　　　　　　　　　＼
　　　　　　　　　　　　　Manβ 4GlcNAcβ 2 4GlcNAcβ→
　　　　　　　　　　　　／
Galβ 4GlcNAcβ 4—Manα 3
Galβ 4GlcNAcβ 2 b. Asialo-oligoside of type lactosamine tetraantenna: receptor of asialoglycoprotein

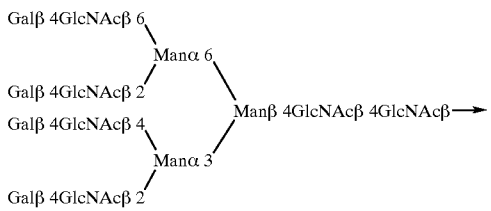

c. Lewis[x]: LECAM 2/3

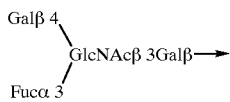

d. Sialyl Lewis[x]: LECAM 3/2

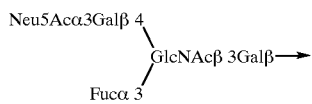

e. Derivative of Lewis[x] sulfate (HNK1): LECAM 1

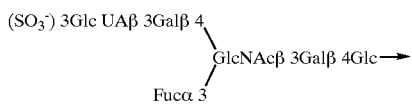

f. Oligomannoside: receptor of mannose

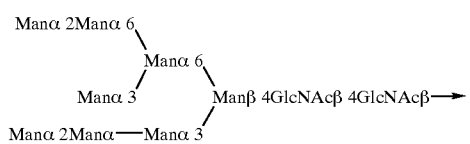

g. Phosphorylated oligomannoside: receptor of mannose 6 phosphate

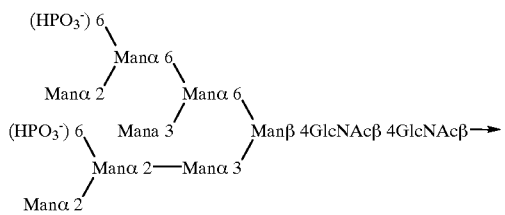

h. Oligosaccharide of sulfated lactosamine type: receptor of sulfated GalNAc 4

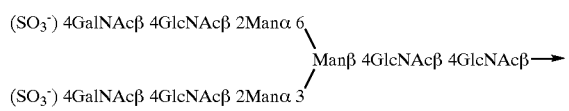

To prepare the compounds of the invention, it is necessary to first prepare the products (derivatives of acylated glycosylamine), which serve in particular as intermediaries for the preparation of said compounds of the invention.

The invention also concerns a procedure of preparation of products (derivatives of acylated glycosylamine) defined above, characterized in that:

one condenses an oligoside having a free terminal reducing sugar, on the nitrogen atom of an intermediary molecule, this nitrogen atom belonging to the amine group, linked to a carbon atom placed in α of a C=O group, the intermediary molecule possibly possessing a lateral chain containing a functional group such as OH, SH, $NH_2$ or COOH, free or protected, this intermediary molecule being chosen from the following intermediary molecules: a amino acid, natural or synthetic, derivative of α amino acid, amino acid in N-terminal position of a peptide, or a peptidic derivative, possibly in presence of a catalyst such as imidazole, in a solvent appropriate for obtaining a derivative of glycosylamine in which the terminal ose of the oligoside conserves its cyclic structure, and in which the semiacetalic hydroxyl is replaced by the α amine of one of the said starting molecules, while the intermediary molecule does not possess a lateral chain containing a functional group such as described above, or a side chain in which the functional group is possibly protected, one acylates the derivative of glycosylamine obtained at the issue of the preceding step by the addition of an organic acid activated by a classical activator such as carbonyl diimidazole, BOP (benzotriazolyl N-oxy-tris(dimethylamino) phosphonium hexafluorophosphate) or HBTU (O-benzotriazol-1-yl-N,N,N',N',tetramethyluronium hexafluorophosphate) to obtain a derivative of N-acylated glycosylamine, followed possibly by a deprotection of the functional group of the said lateral chain, in view of a possible substitution, while the intermediary molecule possesses a side chain containing a carboxylic group, one activates the said carboxylic group to induce an intramolecularly reaction with the said α amine, leading to a cyclization inside the said intermediary molecule, to obtain a derivative of N-acylated glycosylamine.

while the intermediary molecule possesses a side chain containing a carboxylic group, one can add the acylation agent in an active ester form.

The said procedure of preparation of the invention of derivatives of glycosylamine thus includes two steps, one step of condensation of an oligoside on an intermediary molecule to obtain a derivative of glycosylamine, and another step of acylation of said derivative of glycosylamine.

In the step of acylation under consideration in the procedure of the invention, one always uses an activator, in case the intermediary possesses or not a side chain containing a functional group.

Furthermore, it should be specified that the condensation step of the oligoside on the intermediary molecule, to obtain a glycosylamine derivative, as well as the step of acylation of said derivative of glycosylamine are done in presence of appropriate organic solvents.

One of the advantages of using an organic solvent is in particular to allow coupling to the oligoside peptides and derivatives which are slightly or very slightly soluble in water.

These cases can be schematized in the following manner:

1) The intermediary molecule does not possess a side chain containing a functional group, $$\text{Oligoside} + NH_2-CH(R_1)-CO-R_2 \Longrightarrow$$
$$\text{oligosyl-N}-CH-R_1-CO-R_2 +$$
$$R_3-CO_2H + \text{activator}$$
$$\downarrow$$
$$\text{Oligosyl-N(CO}-R_3)-CH(R_1)-CO-R_2$$

$R_1$ representing a residue of an organic molecule without a protected functional group, or $R_1$ being also able to represent H;

$R_2$ representing a residue of an organic molecule such as —CO—R2, either an ester or an amide;

$R_3$ representing a residue of an organic molecule preferably not comprising a free functional group.

The group $R_3$—$CO_2H$+activator can be replaced by the activated product or by an anhydride.

In that which precedes, one can also include the case where $R_3$ possesses a functional group, and in this case, one should refer to paragraph 1a here below.

1a) the intermediary molecule does not possess the side chain containing the functional group, but the agent of acylation is bifunctional, $$\text{oligoside} + NH_2-CH(R_1)-CO-R_2 \Longrightarrow$$
$$\text{oligosyl-NH}-CH(R_1)-CO-R_2 +$$
$$R_3-CO_2H + \text{activator}$$
$$\downarrow$$
$$R_3-CO$$
$$|$$
$$\text{oligosyl-N}-CH(R_1)-CO-R_2$$

$R_3$ representing a residue of an organic molecule comprising a second functional group such as, in particular SH, free or protected, or —$CO_2H$.

Alternatively, the group $R_3$—$CO_2H$+activator can be replaced by the product of activation: $R_3$—CO-activated.

For example, $$R_3-CO-Cl, (R_3-CO)_2O \quad \text{or} \quad R_3-CO-O-N\begin{array}{c}CO-CH_2\\|\\CO-CH_2\end{array}$$

or a cyclic anhyride $$\begin{array}{c}CH_2-CO\\|\\(CH_2)_{\overline{n}}-CO\end{array}\!\!\!\!O,$$

for example with integer n equal to 1, 2, 3 or 4; or a thioester:

$$\begin{array}{c}CH_2-CO\\|\quad\quad|\\(CH_2)_{\overline{n}}-S,\end{array}$$

with whole number n equal to 1, 2, 3 or 4, preferably n=2.

While the acylation of the nitrogen linked to the oligoside is acylated by a cyclic anhydride, the product obtained is of the type:

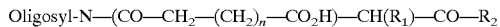
Oligosyl-N—(CO—CH$_2$—(CH$_2$)$_n$—CO$_2$H)—CH(R$_1$)—CO—R$_2$

The carboxylic group is able to be used for a coupling reaction on an organic molecule or a matrix, or a particle possessing a functional group (hydroxyl or amine for example).

While the acylation of the nitrogen linked to the oligoside is acylated by a cyclic thio ester, the product obtained is of the type:

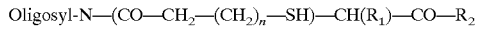
Oligosyl-N—(CO—CH$_2$—(CH$_2$)$_n$—SH)—CH(R$_1$)—CO—R$_2$

The thiol group is able to be used for a coupling reaction on a soluble or insoluble molecule, able to be substituted by a thiol, for example a dithiopyridine or a maleimide derivative.

2) The intermediary molecule possesses a side functional chain and cyclization is not carried out,

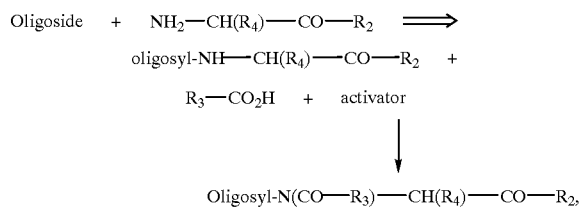

R$_2$ and R$_3$ having the significations indicated above, and R$_4$ representing a residue of an organic molecule possessing a functional group, specifically a carboxylic group, R$_4$ representing specifically CH$_2$—CH$_2$—CO$_2$H.

In this case, one uses preferentially a product of activation of R$_3$—CO$_2$H such as is defined above.

The functional group contained in R$_4$ is available for a condensation reaction or substitution on a soluble or insoluble molecule on a matrice, or a particle comprising of a group able to give a covalent link with the functional group of R$_4$, for example an amine while R$_4$ comprises of a carboxylic group.

3) The intermediary molecule possesses a side chain containing a functional carboxylic group, and one effects a cyclization, and one can fix the molecule on 1 or 2 molecule(s), matrix(ces) or particle(s).

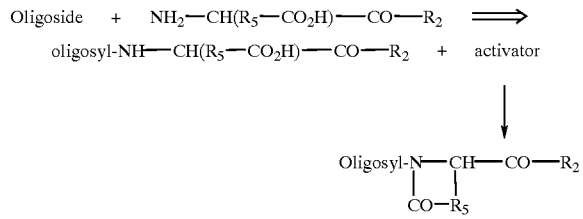

R$_2$ having the significations indicated above,
R$_5$—CO$_2$H being a residue of an organic molecule such as —(CH$_2$)$_n$—CO$_2$H
n being an integer from 1 to 10, preferably 2 or 3.

The glycopeptide thus obtained can be used to react with an existing functional group in a free state or transformed into an active group on R$_2$. For example, if R$_2$ represents the para-nitroanilide group, the NO$_2$ group is reduced to NH$_2$, then transformed into isothiocyanate —N=C=S, which is an excellent reactor with alcohols and to amines.

As examples of intermediary molecules, one can cite:

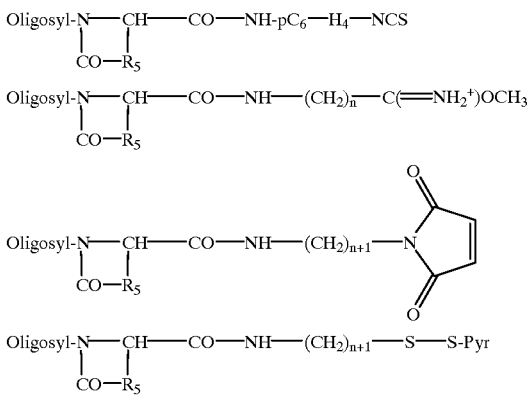

with n=1 to 10.

The invention also concerns the preparation of compounds of the invention, characterized in that one makes a reaction with one or many products (derivatives of glycosylamine acylates) of the invention, carrying either an R group such as defined above, activated or able to be activated, or an A$_i$ group, containing a functional group able to react on a molecule, matrix or particle, P, P' or P" respectively, containing a functional group, to obtain a product of type:

(glycopeptidyl-R)$_n$—P, (glycopeptidyl-B')$_n$—P' or (glycopeptidyl-A$_i$)$_n$—P"

The invention also concerns the preparation of compounds of the invention, characterized in that one can react one or many products (derivatives of acylated glycosylamine) of the invention, carrying in one part an R group such as defined above, activated or able to be activated, and in another part a B' group containing an activated or able to be activated group, or an A$_i$ group containing a functional on molecules, matrices or particles P and P', or molecules, matrices or particles P and P".

The invention also concerns the preparation of compounds of the invention, characterized in that one can react one or many products (derivatives of acylated glycosylamine) of the invention, carrying in one part an R group such as is defined above, activated or able to be activated, in another part a B' group containing an activated or able to be activated group, and an A$_i$ group containing a functional group respectively on molecules, matrices or particles P, B' and P'.

The molecules, matrices or particles entering into the preparation of compounds of the invention are able advantageously to be a natural or synthetic molecule, soluble or not in an organic, aqueous or hydroorganic solvent, a nano particle, a lipid vesicle, a matrix insoluble in an organic aqueous or hydroorganic solvent, a latex bead or a gold bead, etc.

In detail, concerning a procedure according to the invention, the oligoside, having a free reducing sugar, is placed in appropriate solvent, dimethylsulfoxyde, N-methylpyrrolidone or dimethylformamide, for example, in presence of an equal quantity or two equal quantities of a starting molecule chosen from: a natural or synthetic amino acid, a peptide, an amino acid derivative or a peptide derivative.

By appropriate solvent, one designates a solvent allowing both, the solubilisation of compounds to be condensed, and the solubilisation of compounds resulting from the condensation.

The principal product of the reaction is the product of condensation of the type "derivative of glycosylamine": the terminal reducing sugar conserves its cyclic structure, its semiacetalic hydroxyl is replaced by the α amine of the amino acid, by the derivative of the amino acid, or by the amino acid in N terminal position of a peptide or a peptide derivative.

In a second step, the derivative of glycosylamine thus formed is acylated by the addition of an organic activated acid or in the case of a amino acid carrying a lateral chain containing a functional group such as a lateral carboxylic chain, as in the case with glutamic acid or its homologues, by addition of an activator of the carboxylic group.

The product thus formed is a derivative of N-acylated glycosylamine.

The acylated glycosylamine derivatives are isolated by gel filtration chromatography or by any other classic purification technique known in the field.

The derivatives of acylated glycosylamine are then used to substitute a compound (protein, lipid, nucleic acid, oligonucleotide, polylysine, insoluble polymers, latex beads, gold beads, etc.).

One takes advantage of the amino acid fraction, or of the peptide or of a peptide substitute in order to effect the condensation reaction, so that the oligoside conserves all of its properties and its accessibility to serve as substrates or as recognition signals.

According to the following general scheme:

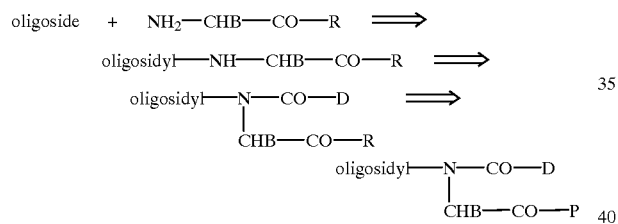

For example, the condensation of lactose with glycylparanitroanilide is expressed

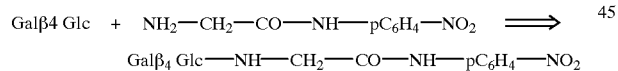

The addition of acetic acid and an organic acid activator leads to:

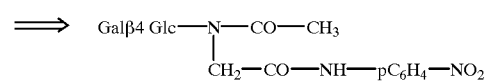

In the example chosen, the nitro group can be further reduced quantitatively into amine, then the amine is transformed quantitatively into isothiocyanate (according to Roche et al. 1983, J. Cell Biochem. 22, 131–140, Monsigny et al. 1984, Biol. Cell 21, 187–196).

The compound thus activated can react in a slightly alkaline medium with an amine carried by a protein, lipid, polymer, (polylysine for example), a solid support comprising amine groups, or an oligonucleotide substituted by an amine, or with an amine carried by a molecule or an appropriate body, such as $NH_2$—P.

One can write, as an example, the following reaction scheme:

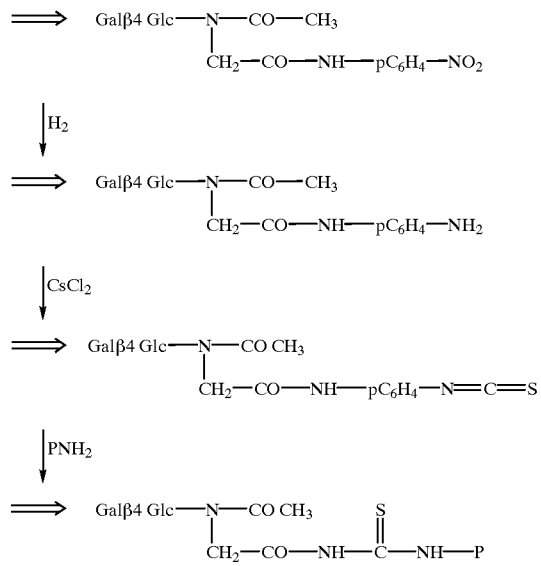

In the case where the amino acid or the derivative is an amino acid possessing a side chain containing a carboxylic group as is the case for glutamate, the reaction is expressed, for example:

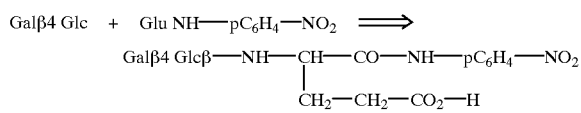

The addition of an activator of carboxylic group leads to the following expected product:

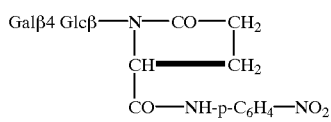

In an analogous way, this compound could be activated and could react on an amine $NH_2$—P, to give the final product:

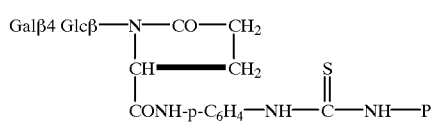

EXAMPLES

Figure 1:
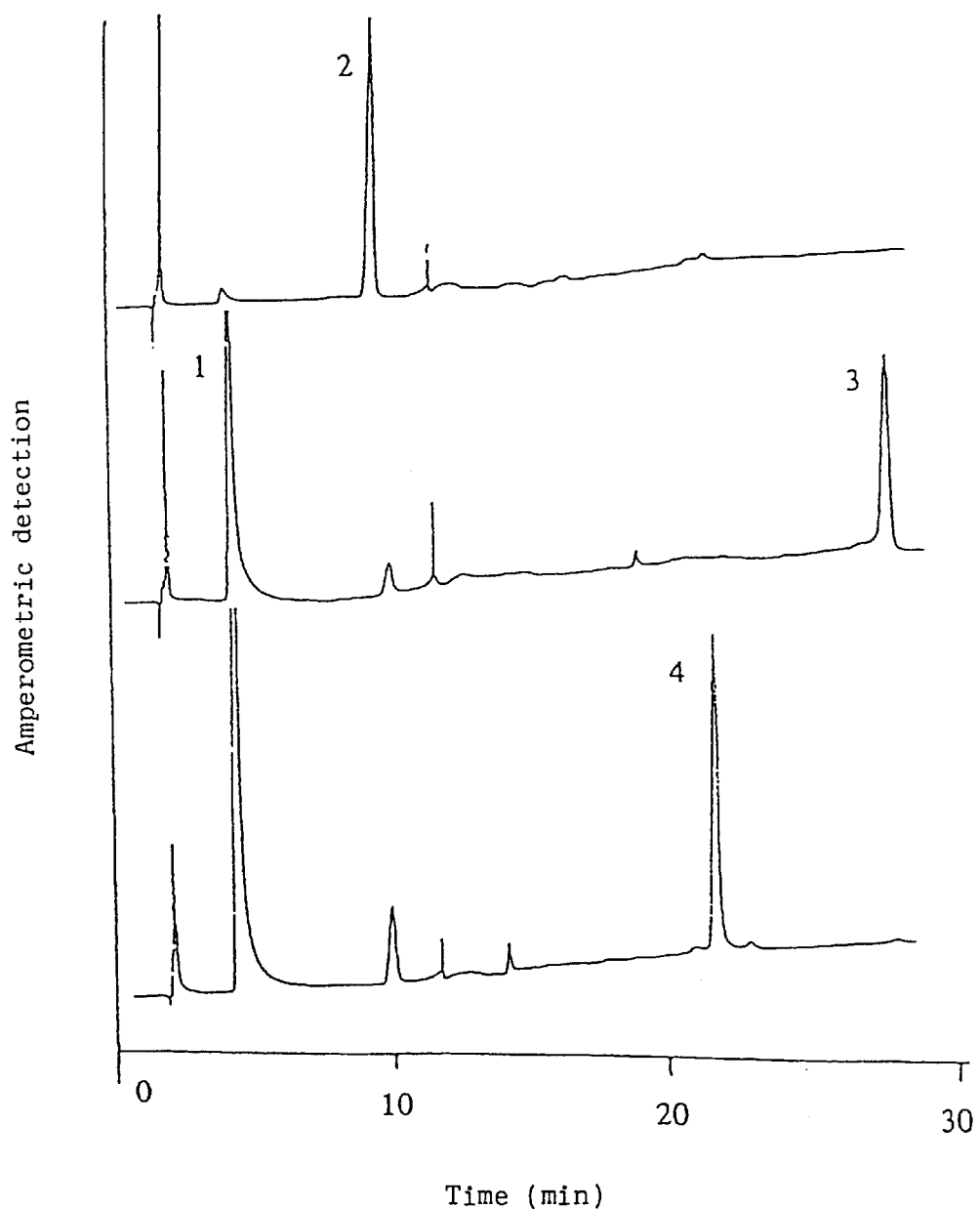
FIG. 1 represents the profile of elution of the β-lactosyl-pyroGlu-pNA obtained by high performance anion exchange chromatography as described in Example 11 below.

Example 1
Preparation of a derivative of acylated glycosylamine: N-acetyl lactosyl β-glycyl-pNA The amido paranitrophenyl (0.1 mmole) and the lactose (0.1 mmole) are dissolved in 1 ml of dimethylsulfoxyde.

The solution is maintained at 50° C. for 48 h. 0.1 mmole of Gly-pNA in 0.5 ml of dimethylsulfoxyde is added at 12 h, 24 h and 36 h. The solution is cooled to 25° C.

Next, 0.44 mmol of BOP, hexafluorophosphate, benzotriazolyl 1 yl-tris (dimethylamino) phosphonium, and 0.44 mmole of diisopropylethylamine acetate is added and the solution is agitated for 3 h at 25° C.

The desired product is purified by molecular sieving on a Ultrogel GF05 column (90×2.3 cm) using 0.1 M acetic acid as a solvent, containing 3% of n-butanol; before the injection, the products of the reaction are diluted by addition of 7.5 ml of solvent of chromatography.

The desired product is eluted first, followed by excess of reactive agents and by dimethylsulfoxyde.

The product: N-acetyl lactosylβ-Gly-pNA is obtained by lyophilisation of the solution eluted from the column.

Example 2
Preparation of a derivative of intramolecularly acylated glycosylamine: N-lactosylβ-pyroGlu-pNA α glutamyl paranitroanilide (Glu-pNA) (0.1 mmole) and lactose (0.1 mmole) are dissolved in 1 ml dimethylsulfoxyde. The solution is maintained at 50° C. for 48 h. 0.1 mmole of Glu-pNA dissolved in 0.5 ml of dimethylsulfoxyde is added at 12 h, 24 h, and 36 h. The solution is cooled to 25° C.

0.44 mmole of BOP is then added and the solution is stirred for 3 h at 25° C.

The desired product is purified under the same conditions as in the preceding example.

Example 3
Preparation of an organic compound, the side chain of which contains a functional group and use of the functional group to form a conjugate with an oligonucleotide The oligoside is incubated in presence of two to four equivalents of the derivative S-(thio-2-pyridine)cysteinyl-p-nitroanilide

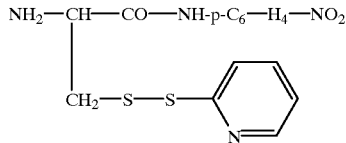

in solution in N-methylpyrrolidone (or in dimethylsulfoxyde or N-dimethylformamide) and in presence of four equivalents of imidazole for 20 h at 50° C. The solution is cooled to 25° C.

Ten equivalents of acetic acid, imidazole, and BOP are then added. The acylation reaction takes place in a half hour.

The glycopeptide is isolated by size exclusion chromatography (column of Ultrogel GF05, for example), in 0.1M acetic acid. The fraction containing the purified glycopeptide is frozen and lyophilized.

The glycopeptide dissolved in 0.1M sodium acetate buffer, pH6, is reduced by addition of an equivalent of TCEP (tris-carboxyethylphosphine) at 25° C. for 30 min (see K. Arar et al.; 1993, Tetrahedron Letters 34, 8087–8090, J. A. Burns et al., 1991, J. Org. Chem., 56, 2648–2650). Added next is an equivalent of an oligonucleotide substituted on its 5' extremity by a substitute terminated by a dithio-2-pyridine group.

The glycopeptide-oligonucleotide conjugate formed has the following general structure:

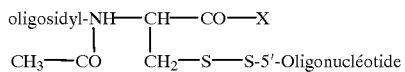

in which X represents NH-p-$C_6$—$H_4$—$NO_2$, and 5' represents the arm bridging the first S dithio-2-pyridine to the primary hydroxyl of the first nucleotide of the oligonucleotide.

Example 4
Preparation of lactosyl-pyroglutamyl-para-nitroanilide (in dimethylsulfoxyde)

The lactose Galβ4Glc (0.15 mmole) is dissolved in 1.25 ml dimethylsulfoxyde ($CH_3$—SO—$CH_3$). 0.30 mmole of Glu-pNA in 1.25 ml dimethylsulfoxyde containing 0.6 mmole imidazole (pNA=para nitro-anilide) is added. The solution is kept at 50° C. for 20 h, then cooled to 25° C. More than 95% of the lactose is transformed into glycopeptide: lactosyl-Glu-pNA.

0.33 mmole of BOP and 0.6 mmole of imidazole is added. The solution is stirred for 30 min at 25° C. More than 95% of the glycopeptide is cyclized into lactosyl-pyroglutamyl-paranitro-anilide:

pGlu is: the residue pyroglutamyl

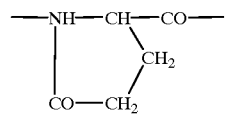

Example 5
Preparation of lactosyl-pyroglutamyl-p-nitroanilide (in N-methylpyrrolidone)

The lactose Galβ4Glc (0.15 mmole) is dissolved in 1.25 ml N-methylpyrrolidone of the formula:

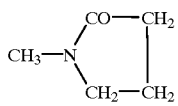

0.3 mmole of Glu-pNA in 1.25 mmole of N-methylpyrrolidone containing 0.6 mmole of imidazole is added. The solution is kept at 50° C. for 20 h then cooled to 25° C. More than 95% of the lactose is transformed into glycopeptide: lactosyl-Glu-pNA. 0.33 mmole of BOP and 0.6 mmole of imidazole are added. The solution is stirred for 30 min at 25° C. More than 95% of the glycopeptide is cyclized into lactosyl-pyroglutamyl-p-nitro-anilide.

The analyses are done by high pressure liquid chromatography on a column on a Dionex apparatus, equipped with an amperometric detector. The results are calculated in relation to an internal control (sorbitol) added to the initial lactose solution.

The time of retention of the compounds under standard conditions, expressed in minutes, are:

| | |
|---|---|
| Lactose | 9.9 ± 0.1 |
| Lactosyl-Glu-pNa | 21.4 ± 0.1 |
| Lactosyl-p-Glu-p-NA | 16.2 ± 0.1 |
| Imidazole | 4.3 ± 0.1 |
| Sorbitol | 2.7 ± 0.1 |

Example 6

Preparation of a compound of the formula

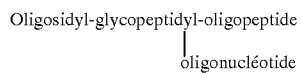

The preparation may be done according to the following reaction schema.

The original product indicated hereafter, can be obtained as previously indicated, in relation to the preparation of the products of the invention.

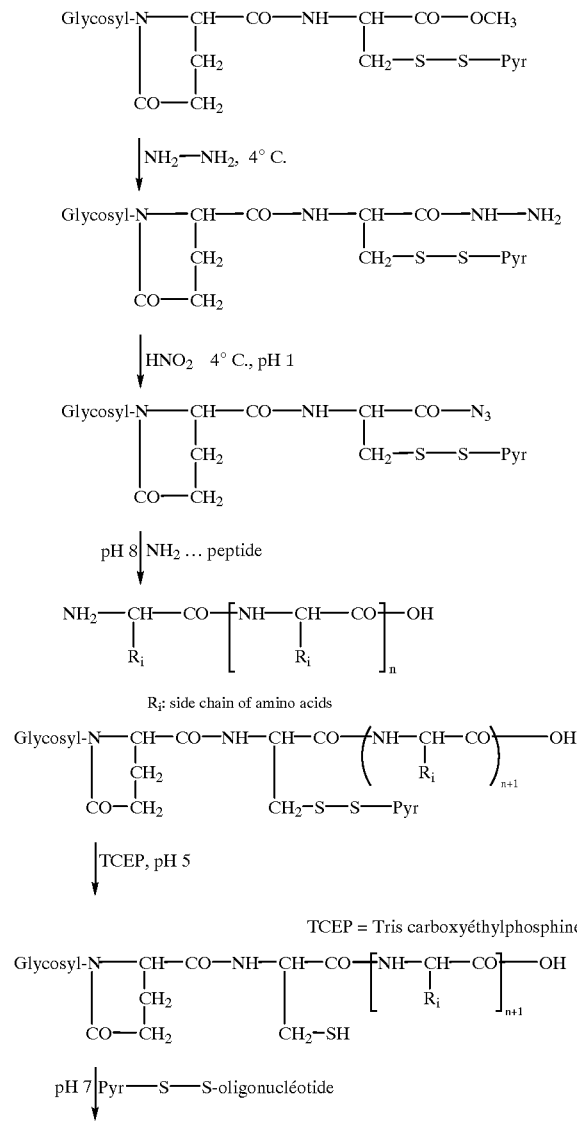

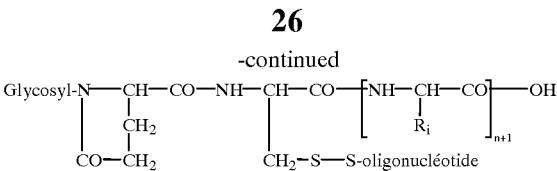

The example chosen corresponds to the preparation of a derivative of oligonucleotide, so that this derivative presents a biological activity in relation to the sequence of the oligonucleotide chosen (the oligonucleotide sense, antisense, antigen, bait, etc., is specific to a cellular or viral element of nucleic acid or protein nature), the oligoside allows the derivative to be selectively recognized by certain cells which possess a membrane receptor (lectin) having an affinity for the chosen oligoside. The peptide allows the derivative—once inside the endosomes (intracellular vesicles), thanks to the mechanism of endocytosis due to the membrane lectin—to penetrate the cytosol and then the nuclear compartments.

The oligonucleotide is an oligomer containing between 10 to 40 nucleotides, preferably 20 to 25. The oligopeptide is an oligomer comprising between 20 to 40 amino acids, preferably 20 to 25. This type of derivatives corresponds to a line of compounds able to be utilized as drugs.

Example 7

Preparation of a compound of formula

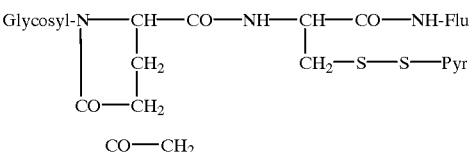

The preparation of this compound can be made following the following reaction schema:

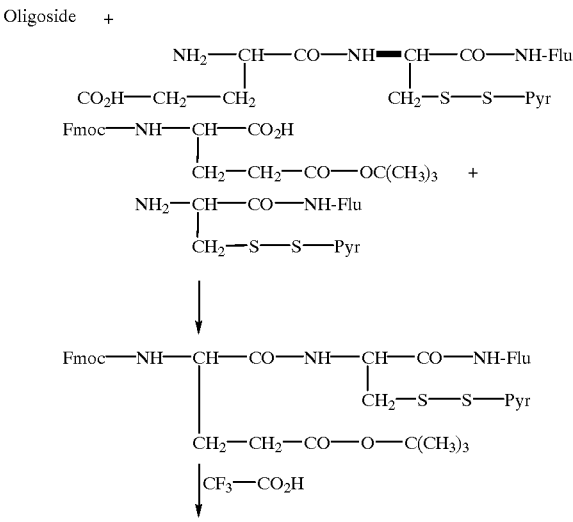

27

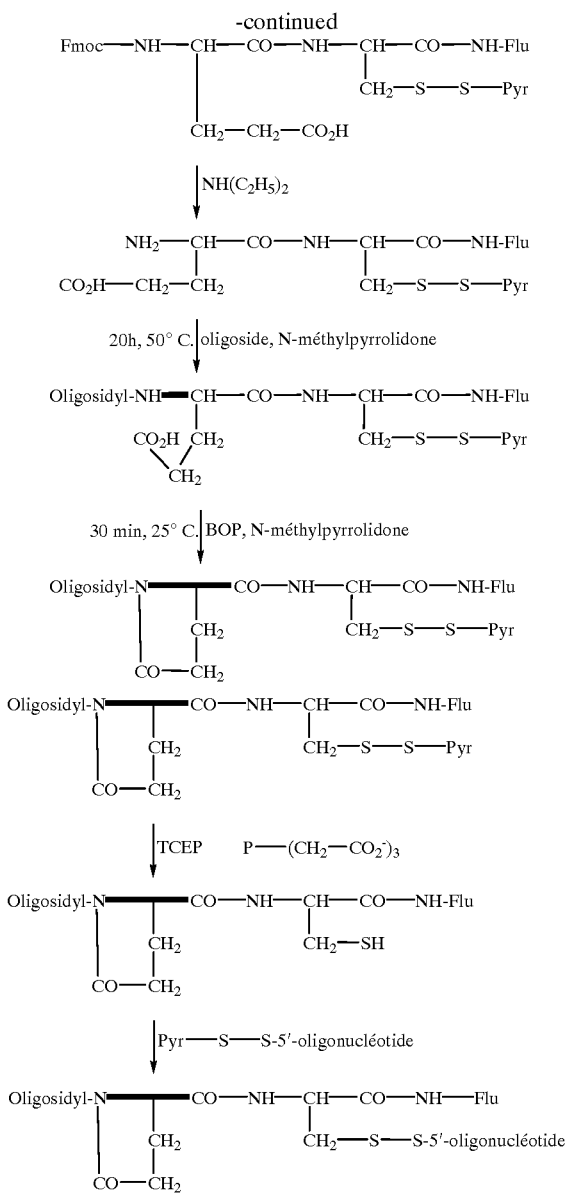

The example chosen corresponds to the preparation of a derivative of glycopeptidic fluorescent of general utilisation.

The residue of fluoresceine allows for an utilisation of glycopeptides for the purposes of localisation, visualisation, in a general manner, for the purposes of analysis, specifically in fluorescence microscopy.

The glycopeptidic fluorescent derivative linked to a oligonucleotide can also be used as an antiviral or anticancerous agent, in order to allow at the same time the study of the biological activity of the derivative and its intracellular activity as well as its pharmacokinetic activity in the animal.

In this example, the disulfure bridge is present in the original compound on an Ai residue of the general formula.

28

Example 8
Preparation of a compound of formula

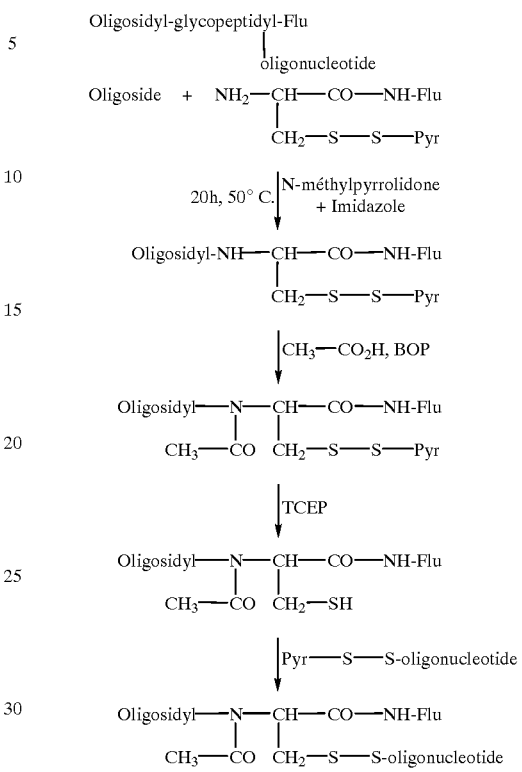

What has been said regarding the glycopeptidic derivative of example 7 also applies to this example. It should be noted that in example 8 herein considered, the disulfure bridge is present in the original compound on the Z chain of the general formula.

Example 9
Preparation of glycosylated derivatives of gluconoylated polylysine The gluconoylated polylysine is used to transfer genes into animal cells. Substitution of the gluconoylated polylysine by one or many glycopeptides allows to make selective the transfer of genes.

The glycosylated derivatives of the gluconoylated polylysine penetrate preferably (100 to 1000 times more) in cells which express on their surface a lectin (receptor of oligosides), which specifically recognizes the oligoside of the glycopeptide linked to the gluconoylated polylysine.

a) Link of a glycopeptide to the gluconoylated polylysine via a disulfide bridge.

The gluconoylated polylysine (degree of polymerisation 190; containing 60 gluconoyle residues), is substituted by a derivative of the dithiopyridine; the polymer (20 mg; 0.33 $\mu$mol) is dissolved in 0.5 ml of dimethylsulfoxyde.

1 $\mu$mol (312 $\mu$g) of N-succinimidyl 3-(2-pyridyldithio) propionate and 20 $\mu$mol (3.6 $\mu$l) of diisopropylethylamine are added. The solution is stirred at 20° C. for 15 h. The polymer is precipitated by addition of 10 volumes of isopropanol; the precipitate is recovered after centrifugation (1 800 g, 15 min).

After washing with isopropanol, the polymer is dissolved in a sodium phosphate buffer, 0.1 M at pH 7.2 (1 ml).

The glycopeptide: oligosylpyroglutamyl amido ethyldithiopyridine:

Galβ4Glcβ-pyroglutamyl-NH—(CH$_2$)$_2$—S—S-pyridine (1 μmol) is treated with 1 μmole of TCEP [(triscarboxyethylphosphine: P(CH$_2$—CH$_2$—CO$_2$$^-$)$_3$)] in a sodium phosphate buffer, 0.1 M (1 ml), for 1 h at 20° C. This solution is added to the solution of gluconoylated polylysine substituted with pyridyldithiopropionate. After 1 h at 20° C., the polymer is precipitated by addition of 10 volumes of isopropanol. The precipitate is recovered after centrifugation (1 800 g, 15 min) and washed with isopropanol, then dissolved in water and lyophilized.

The yield of the coupling reaction under the used conditions is equal or superior to 90%.

The reactions which are used in this preparation are derived of the ones described in Midoux, P., Mendes, C., Legrand, A., Rammond, J., Mayer, R., Monsigny, M. and Roche, A. C., 1993: Specific gene transfer mediated by lactosylated poly-1-lysine into hepatoma cells. Nucleic Acid Research, 21: 871–878, and in Arar, K., Monsigny, M., and Mayer, R., 1993: Synthesis of oligonucleotide peptide conjugates containing a KDEL signal sequence. Tetrahedron Letters, 34: 8087–8090.

b) Link of a glycopeptide to the gluconoylated polylysine via a thiourea link.

The gluconoylated polylysine (degree of polymerisation 190; containing 60 residues of gluconoyle), is substituted by an activated glycopeptide in the form of phenylisothiocyanate.

The glycopeptide oligosylpyroglutamyl p-nitroanilide is reduced to a p-amino anilide derivative which is then activated into a p-cyanato-anilide derivative:

Galβ4Glcβ-pyroglutamyl-NH-p-C$_6$H$_4$—NCS following a protocol adapted to that described in Roche, A. C., Barzilay, M., Midoux, P., Junqua, S., Sharon, N. and Monsigny, M. (1983): Sugar specific endocytosis of glycoproteins by Lewis lung carcinoma cells., J. Cell. Biochem., 22: 131–140.

The cyanato-anilide derivative (1 μmole) is dissolved in dimethylsulfoxyde (1 ml) containing 1 μmole of gluconoylated polylysine and 4 μmoles of diisopropyl ethylamine. The solution is stirred at 20° C. for 24 h. The glycosylated polymer is precipitated by addition of 10 volumes of isopropanol; the precipitate is recovered after centrifugation, washed with isopropanol, and finally dissolved in water and lyophilized.

In the conditions described, the coupling yield of the glycopeptide to the gluconoylated polylysine is better than to 95%

Example 10
Preparation of a glycopeptide (oligosylpyroglutamyl-p-nitroanilide) in dimethylformamide as solvent The α glutamyl-p-nitroanilide (0.2 mmoles) and the lactose (0.1 mmole) are dissolved in 1 ml of dimethylformamide, in presence of 0.2 mmoles of imidazole. The solution is kept at 50° C. for 8 h.

The solution is cooled to 25° C., and 0.2 mmole of BOP and 0.2 mmole of imidazole are added and left for 30 min. Under these conditions, more than 95% of the original oside is transformed into glycopeptidic derivative. The purification is identical to that described in using the other solvents.

Example 11

The purity of the prepared product at example 2 (N-lactosylβ-pyroGlu-pNA, which is hereafter designated also as β-lactosyl-pyroGlu-pNA) was assessed by high performance anion exchange chromatography and by amperometric detection (HPAE-PAD) on an apparatus of trademark Dionex.

Concerning this technique, one proceeds as follows:

The osides are ionized in alkaline medium (0.1M sodium hydroxyde) in the form of polycoolates. Their separation on a cationic resin (immobilized ammonium ions ) is very efficient. The detection of the osides is advantageously effected by an amperometric measure in pulse current. The apparatus used (Dionex) was specially built to carry out the chromatography in alkaline medium and the amperometric detection on line.

The retention times (t$_r$) of the different products were characterized (see FIG. 1):

| Pic | t$_r$ (min) | Compound |
|---|---|---|
| 1 | 4,4 | Imidazole |
| 2 | 10,0 | Lactose |
| 3 | 27,5 | β-lactosyl-Glu-pNA |
| 4 | 22,9 | β-lactosyl-pyroGlu-pNA |

In FIG. 1:

the first curve (from the top of the sheet) corresponds to the injection of only lactose, the second curve corresponds to the injection of the reaction mixture after 12 h, the third curve corresponds to the injection of the reaction mixture after 12 hours+30 minutes of cyclisation.

Example 12
Preparation of a derivative of intramolecularly acylated glycosylamine: Lewis$^A$/Lewis$^X$-pyroGlu-pNA Lewis$^A$/Lewis$^X$ (0.06 mmole) is dissolved in 1 ml of dimethylformamide. 0.12 mmole of Glu-pNA then 0.24 mmole of imidazole are added. The solution is kept at 50° C. for 15 h. The stabilisation of the glycopeptide is obtained by adding, after reaction medium brought to 20° C., 0.13 mmole of BOP and 0.24 mmole of imidazole. After 30 min, the glycopeptide is cyclized into Lewis$^A$/Lewis$^X$-pyroGlu-pNA. The reaction is followed by HPAE-PAD.

Synthesis of Lewis$^A$/Lewis$^X$-pyroGlu-pNA. Profiles of Dionex elution. The retention times (t$_r$) of different products where characterized (see FIG. 2):

| Pic | t$_r$ (min) | Compound |
|---|---|---|
| 1 | 4.5 | Imidazole |
| 2 | 8.9/9.4 | Lewis$^A$/Lewis$^X$ |
| 3 | 22.5/22.7 | Lewis$^A$/Lewis$^X$-Glu-pNA |
| 4 | 17.4/17.6 | Lewis$^A$/Lewis$^X$-pyroGlu-pNA |

Figure 2:
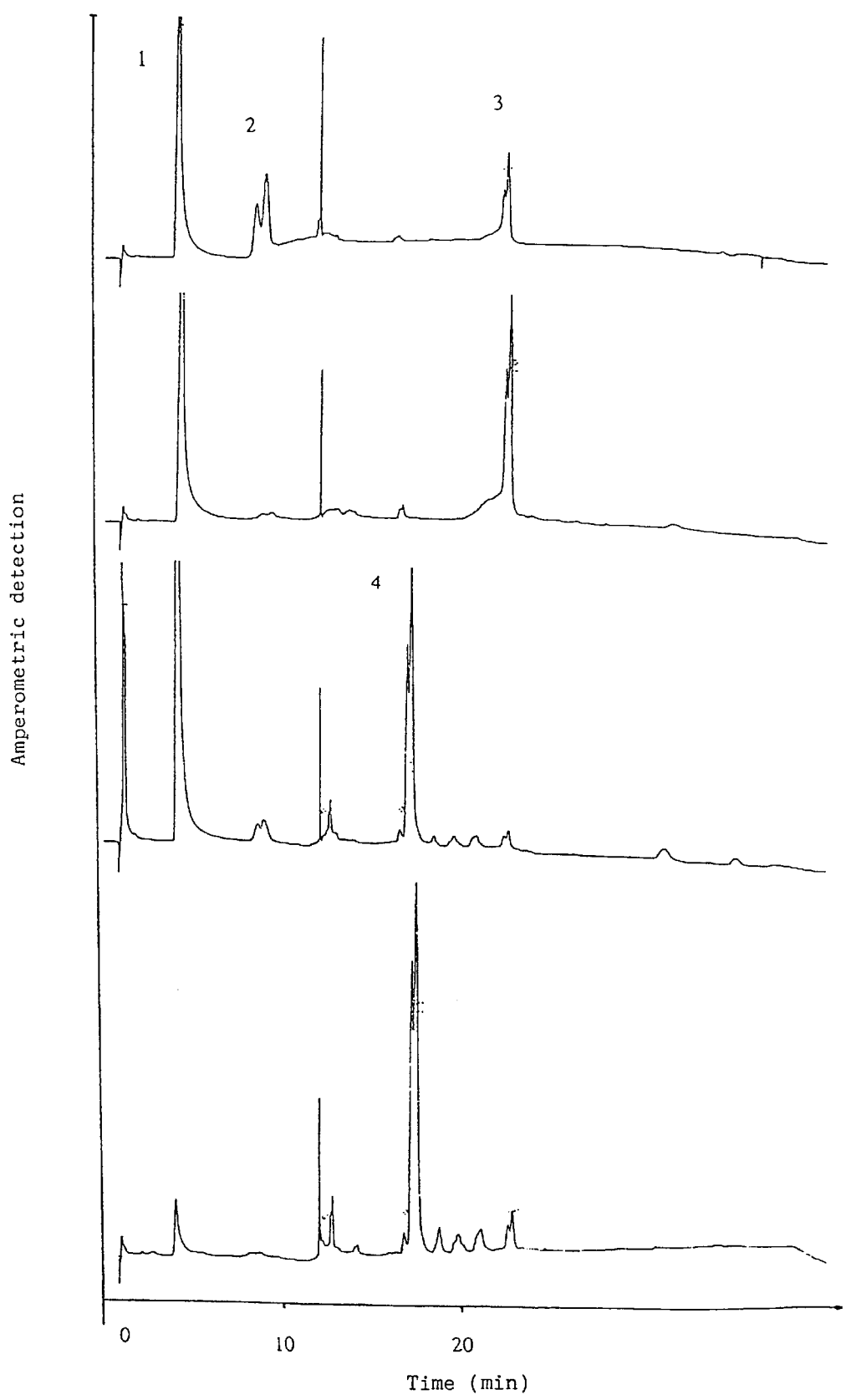
FIG. 2 represents the profile elution of the Lewis$^A$/Lewis$^X$-pyroGlu-pNA obtained by high performance anion exchange chromatography as described in Example 12 below.

In FIG. 2:

the first curve (from the top of the sheet) corresponds to the injection of the reaction mixture after 15 minutes, the second curve corresponds to the injection of the reaction mixture after 15 hours, and the third curve corresponds to the injection of the reaction mixture after 15 hours+30 minutes of cyclization.

Purification of the glycopeptide

After the synthesis described above, one proceeds to the purification in two steps:

by size exclusion on a Trisacryl GF05 (100×2.3 cm) column with a flow rate of 10 ml/h, eluted by an aqueous solution containing 0.1 M acetic acid and 3% n-butanol; this first step allows the elimination of the non-reacted oligosaccharides as well as the excess BOP=hexafluorophosphate od benzotriazolyl-oxy-tris (dimethylamino)phosphonium, and the Glu pNA, by ethanolic precipitation (90%), during which the sample is maintained at 4° C. for 24 h; this second step allows the elimination of the excess imidazole.

The purification is followed by HPAE-PAD.

In FIG. 2, the fourth curve corresponds to the injection of the product Lewis$^A$/Lewis$^X$-pyroGlu-pNA purified by size exclusion followed by an ethanolic precipitation ($t_r$: 17.4/17.6).

Characterization of the glycopeptide (Lewis$^A$/Lewis$^X$-pyroGlu-pNA)

An analysis in $^1$H RMN at 300 MHz was conducted.

The Lewis$^A$/Lewis$^X$-pyroGlu-pNA was dissolved in D$_2$O (6.10$^{-3}$ mole/l). Lewis$^A$ possesses a terminal galactose bound in 3 and a fucose terminal bound in 4 on the N-acetylglucosamine. Lewis$^X$ possesses a galactose terminal bound in 4 and a fucose terminal bound in 3 on the N-acetylglucosamine. Spectrum analysis allowed the identification of the characteristic protons:

common to the 2 glycopeptides: 8.33 and 7.79 (4H, 2d, H aromatic); 4.90 (2H, m, H5 αFuc); 4.67 (1H, d, J$_{1,2}$, 7.32 Hz, H1 βGlcNAc); 4.37 (1H, d, J$_{1,2}$ 7.42 Hz H1 βGal$^{int}$); 4.16 (1H, s, H4 βGal$^{int}$); 2.83 (2H, m, γCH$_2$ pyroGlu); 2.33 (2H, m, β and β'CH$_2$ pyroGlu); 2.05 and 2.04 (6H, 2s, CH$_3$ Ac GlcNAc); 1.22 and 1.21 (6H, 2s, CH$_3$ Fuc);

specific of Lewis$^A$: 5.05 (1H, d, H1 αFuc); 4.53 (1H, d, H1 βGal);

specific of Lewis$^X$: 5.24 (1H, d, J$_{1,2}$, 7.2 Hz, H1 αFuc); 4.50 (1H, d, H1 βGal).

Example 13

Lewis$^B$-pyroGlu-pNA and oligoH-pyroGlu-pNA have been prepared as indicated in example 12.

As reviewed hereafter, the analysis of glycopeptides obtained includes that of β-lactosyl-pyroGlu-pNA (N-lactosylβ-pyroGlu-pNA) and Lewis$^A$/Lewis$^X$-pyroGlu-pNA.

Analysis of glycopeptides (Dionex apparatus)

Separation by anion exchange chromatography. Column CarboPac PA1 (4×250 mm) Flow rate: 1 ml/min. Detection by pulse amperometry. Work done at room temperature.

For good separation, a sodium acetate gradient is used:

| Time (min) | NaOH 100 mM | NaOH 100 mM CH$_3$COONa 1M |
|---|---|---|
| 0 | 100 | 0 |
| Injection 0,1 | 100 | 0 |
| 5 | 100 | 0 |
| 15 | 80 | 20 |
| 30 | 0 | 100 |
| 35 | 0 | 100 |
| 40 | 100 | 0 |

Retention times expressed in minutes:

| Imidazole | 4.4 ± 0.1 |
|---|---|
| Lactose | 10.0 ± 0.1 |
| β-lactosyl-Glu-pNA | 27.5 ± 0.1 |
| β-lactosyl-pyroGlu-pNA | 22.9 ± 0.1 |
| Imidazole | 4.5 ± 0.1 |

| Lewis$^A$/Lewis$^X$ | 8.9-9.4 ± 0.1 |
|---|---|
| Lewis$^A$/Lewis$^X$-Glu-pNA | 22.5/22.7 ± 0.1 |
| Lewis$^A$/Lewis$^X$-pyroGlu-pNA | 17.4/17.6 ± 0.1 |
| Imidazole | 4.4 ± 0.1 |
| Lewis$^B$ | 7.3 ± 0.1 |
| Lewis$^B$-Glu-pNA | 19.7 ± 0.1 |
| Lewis$^B$-pyroGlu-pNA | 16.6 ± 0.1 |
| Imidazole | 4.5 ± 0.1 |
| OligoH | 8.2/8.7 ± 0.1 |
| OligoH-Glu-pNA | 23.8 ± 0.1 |
| OligoH-pyroGlu-pNA | 18.9 ± 0.1 |

What is claimed is:

1. Compounds of the general formula (I)

$$\begin{array}{c} \text{oligosidyl-N}-\text{CO}(-\text{D})_a \\ | \quad\quad | \\ (Z)_b-\text{CH}[-(\text{CH}_2)_p]_j \\ | \\ \text{COX} \end{array} \quad (I)$$

in which:
a=0 or 1,
j=0 or 1,
b=0 or 1,
p=2 to 4,
provided that
a=b=0, when j=1, which leads to the presence of a cyclic molecule,
or a=b=1, when j=0 which implies the absence of the (CH$_2$)$_p$ group, D represents a residue of an organic acid of the formula ECO$_2$H, wherein E is H or an alkyl chain of 1 to 10 carbon atoms, Z represents
B, B being H, an alkyl of 1 to 10 carbon atoms or a side chain of an α amino acid, or
B'—P', B' being an alkylene chain of 1 to 10 carbon atoms or a side chain of an α amino acid, the said chains containing a group derived from a functional group able to be activated, P' having the significations indicated hereafter, X represents:

• group [NH—(A$_i$)—CO]$_{\overline{m}}$—Q,
  $\quad\quad\quad\quad |$
  $\quad\quad\quad\quad (P'')_k$

• or the group [NH—(A$_i$)—CO]$_{\overline{m}}$—P,
  $\quad\quad\quad\quad\quad |$
  $\quad\quad\quad\quad\quad (P'')_k$

• or the group [NH—(A$_i$)—CO]$_{\overline{m}}$—R—P,
  $\quad\quad\quad\quad\quad |$
  $\quad\quad\quad\quad\quad (P'')_k$ m being an integer from 0 to 10, k=0 or 1

Q representing OH, OCH$_3$, OCH$_2$—C$_6$H$_5$, O—C$_6$H$_5$, O—C$_6$F$_5$, O-pC$_6$H$_4$—NO$_2$, or $$\begin{array}{c} \text{O}-\text{N}-\text{CO}-\text{CH}_2 \\ \quad\quad \diagdown \quad\quad | \\ \quad\quad\quad \text{CO}-\text{CH}_2 \end{array}$$

R representing a group possessing an alcohol, phenol, thiol, or amine function, $A_i$ representing an organic radical, P, P', and P" are identical or different and represent:
- a matrix support for affinity chromatography;
- a bead of gold, or latex;
- a protein;
- a lipid;
- oligonucleotides; or
- a polymer;

P, P' and P" possessing at least one chemical function allowing a condensation reaction by reaction with an oligopeptide, wherein the oligosidyl moiety of formula (I) comprises a terminal cyclic hemiacetal residue in which the hemiacetalic hydroxy is replaced by the N of formula (I), thereby to render said hemiacetal non-reducing.

2. Compound according to claim 1, characterized in that P' or P" represents an oligonucleotide, or R represents fluoresceine or a derivative thereof or another fluorescent derivative, and P' or P" represents an oligonucleotide.

3. Compounds according to claim 1, of the general formula (II)

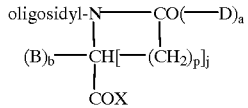
(II)

in which:
X represents:
either the group $[NH-(A_i)-CO]_m-P$,
or the group $[NH-(A_i)-CO]_m-R-P$; and
P represents:
- a matrix support for affinity chromatography;
- a bead of gold or latex;
- a protein,
- an oside receptor,
- a lipid; or
- oligonucleotides, wherein a, j, b, p, D, B, m, $A_i$, and R are as defined in claim 2.

4. Compounds according to claim 1, of the general formula (III)

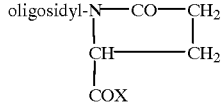
(III)

in which X represents $[NH-(A_i)-CO]_m-P$ or $[NH-(A_i)-CO]_m-R-P$, and wherein R, $A_i$, m, and P are as defined in claim 1.

5. Compounds according to claim 1, of the general formula (IV)

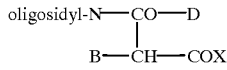
(IV)

in which X represents $[NH-(A_i)-CO]_m-P$ or $[NH-(A_i)-CO]_m-R-P$, and wherein R, $A_i$, D, m, and P are as defined in claim 1.

6. Compounds according to claim 1, of the general formula (V)

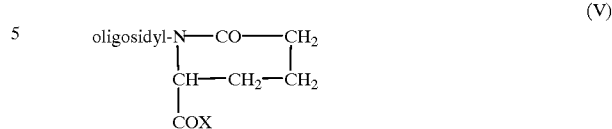
(V)

in which X represents $[NH-(A_i)-CO]_m-P$ or $[NH-(A_i)-CO]_m-R-P$, and wherein R, $A_i$, m, and P are as defined in claim 1.

7. Products of a general formula (Ia)

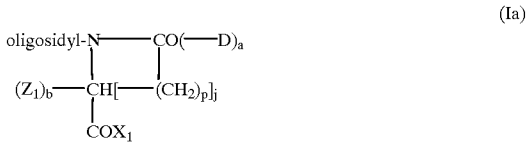
(Ia)

in which:
a=0 or 1,
j=0 or 1,
b=0 or 1,
p=2 to 4,
provided that
a=b=0, when j=1, which leads to the presence of a cyclic molecule,
or a=b=1, when j=0 which implies the absence of the $(CH_2)_p$ group, D represents a residue of an organic acid of the formula $ECO_2H$, wherein E is H or an alkyl chain of 1 to 10 carbon atoms, $Z_1$ represents
B, B being chosen from among: H, an alkyl chain of 1 to 10 carbon atoms, and a side chain of an α amino acid, or
B', B' being chosen from among: an alkylene chain of 1 to 10 carbon atoms, or a side chain on an α amino acid, said chains containing a functional group, $X_1$ represents
the group $[NH-(A_1)-CO]_m-R$,
or $[NH-(A_1)-CO]_m-Q$ R representing a group possessing an alcohol, phenol, thiol, or amine function, Q representing $OH$, $OCH_3$, $OCH_2-C_6H_5$, $O-C_6H_5$, $O-C_6F_5$, $O-pC_6H_4-NO_2$, or

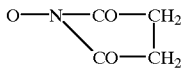

m being an integer from 1 to 10,
$A_i$ represents an organic radical, wherein the oligosidyl moiety of formula (Ia) comprises a terminal cyclic hemiacetal residue in which the hemiacetalic hydroxy is replaced by the N of formula (Ia), thereby to render said hemiacetal non-reducing.

8. Compounds or products according to claim 7, characterized in that R represents the following radicals:

OH, O—CH₂—C₆H₅, O—C₆H₅, O—C₆F₅, O-pC₆H₄—NO₂,

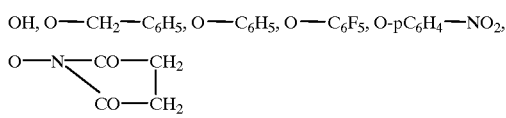

—NH—pC₆H₄—N=C=S and its precursors: —NH—pC₆H₄—NO₂ —NH—pC₆H₄NH₂ —NH—CH₂—(CH₂)$_m$—C(=NH₂⁺)OCH₃ —NH—CH₂—(CH₂)$_m$—CN —NH—CH₂—(CH₂)$_m$—CH₂—NH—CO—CH₂—(CH₂)$_m$—C(=NH₂⁺)$^{OCH}$₃ —NH—CH₂—(CH₂)$_m$—CH₂—NH—CO—CH₂—(CH₂)$_m$—CN

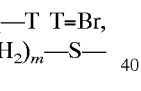

—NH—CH₂—(CH₂)$_m$—CH₂—NH—CO—CH₂—T  T=Br, I, Cl —NH—CH₂—CH₂—NH—CO—CH₂(CH₂)$_m$—S—S—Pyr

—NH—CH₂—(CH₂)$_m$—CH₂—S—S—Pyr

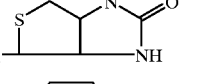

—NH—(CH₂)$_m$—pC₆H₄OH  —NH—CH₂—(CH₂)$_m$—CH₂—NH—CO—(CH₂)$_m$—pC₆H₄OH

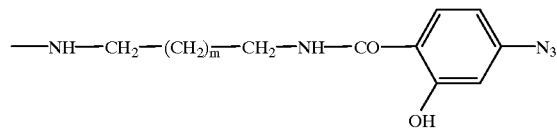

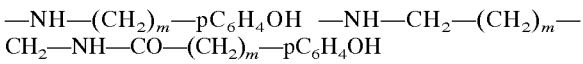

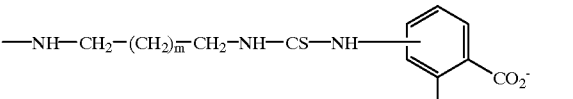

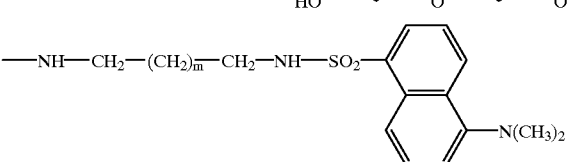

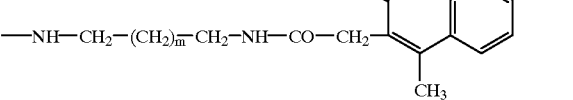

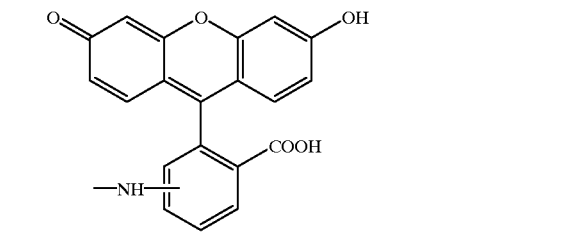

9. Compounds according to claim 7, characterized in that the oligosidyl residue is an oligosaccharide comprised of from 2 to 50 oses and is chosen from:

| | |
|---|---|
| lacto-N-tetraose | Galβ GlcNAcβ 3 Gal β 4 Glc |
| neolacto-N-tetraose | Galβ 4 GlcNAcβ 3 Gal β 4 Glc |
| Group H | Fuc α 2 Galβ 3 Galβ 4 Glc |
| Lewis$^a$ | Galβ 3 GlcNAcβ 3 Gal β 4 Glc |
| | Fuc α 4-↑ |
| Lewis$^x$ | Galβ 4 GlcNAcβ 3 Galβ 4 Glc |
| | Fuc α 3-↑ |
| Lewis$^b$ | Fucα 2 Galβ 3 GlcNAc β 3 Galβ 4 Glc |
| | Fuc α 4-↑ |
| Lewis$^y$ | Fuc α 2 Galβ 4 GlcNAcβ 3 Galβ 4 Glc |
| | Fuc α 3-↑ |
| Disialolacto-N-tétraose | Neu 5 Acα 3 Gal β 3 GlcNAc β 3 Gal β 4 Glc |
| | Neu 5Acα 6-↑ |

Three antenna complex of the formula:

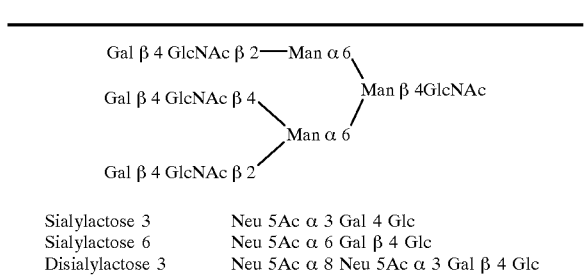

| Sialylactose 3 | Neu 5Ac α 3 Gal 4 Glc |
| --- | --- |
| Sialylactose 6 | Neu 5Ac α 6 Gal β 4 Glc |
| Disialylactose 3 | Neu 5Ac α 8 Neu 5Ac α 3 Gal β 4 Glc | simple or complex osides recognized by the lectin membranes, and chosen from:

a. Asialo-oligoside of lactosamine triantenna: receptor of asialoglycoprotein

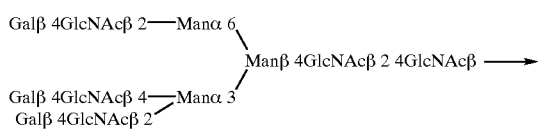

b. Asialo-oligoside of lactosamine tetraantenna: receptor of asialoglycoprotein

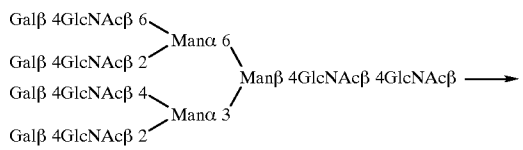

c. Lewis$^x$: LECAM 2/3

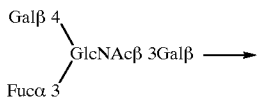

d. Sialyl Lewis$^x$: LECAM 3/2

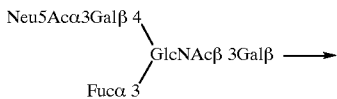

e. Derivative of Lewis$^x$ sulfate (HNK1): LECAM 1

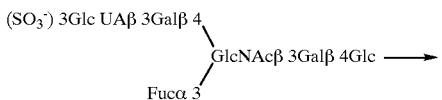

f. Oligomannoside: receptor of mannose

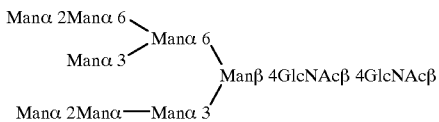

g. Phosphorylated oligomannoside: receptor of mannose 6 phosphate

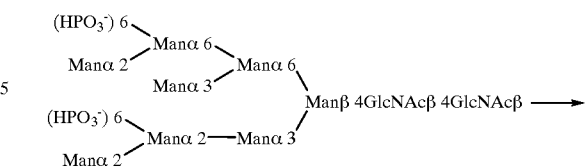

h. Oligosaccharide of sulfated lactosamine receptor of sulfated GalNAc 4

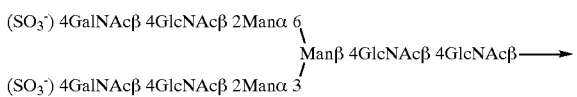

10. Process for preparing compounds according to claim 7, comprising:

(a) condensing an oligoside having a free reducing sugar, on the nitrogen atom of an intermediary molecule, said nitrogen atom belonging to an amine group, linked to a carbon atom placed in α of a C=O group, in presence of a catalyst and in a solvent appropriate for obtaining a derivative of glycosylamine in which the terminal ose of the oligoside conserves its cyclic structure, and in which the semiacetalic hydroxyl is replaced by the α amine of one of said intermediary molecules, wherein if the intermediary molecule does not possess a side chain containing a functional group, acylating the derivatives of glycosylamine obtained at the end of step (a) by the addition of an organic acid activated by an activator to obtain a derivative of N-acylated glycosylamine, or wherein if the intermediary molecule possesses a side chain containing a carboxylic group, activating the carboxylic group to intramolecularly react with said α amine, leading to a cyclization inside the intermediary molecule, to obtain a derivative of N-acylated glycosylamine.

11. The process of claim 10, where in step (a) the intermediary molecule is selected from the group consisting of: an α amino acid, a natural or synthetic, derivative of said α amino acid, an amino acid in N-terminal position of a peptide, and a peptidic derivative.

12. Products according to claim 7, of the general formula (IIa)

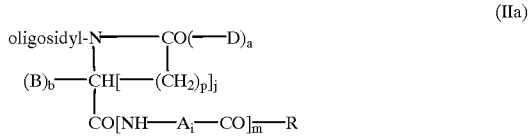

wherein a, j, b, p, D, B, m, $A_i$, and R are as defined in claim 7.

13. Products according to claim 7, of the general formula (IIIa)

(IIIa)

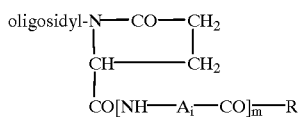

wherein $A_i$, m, and R are as defined in claim 7.

14. Products according to claim 7, of the general formula (IVa)

(IVa)

oligosidyl-N—CO—D
    |
B—CH—CO[NH—A$_i$—CO]$_{\overline{m}}$—R wherein D, B, m, $A_i$ and R are as defined in claim 7.

15. Products according to claim 7, of the general formula (Va)

(Va)

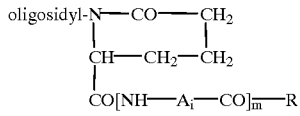

wherein $A_i$, m, and R are as defined in claim 7.

16. Products of a general formula (VI)

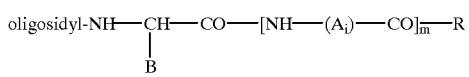

in which:

B is chosen from among: H, an alkyl chain of 1 to 10 carbon atoms, and a side chain of an α amino acid, R represents a group possessing an alcohol, phenol, thiol, or amine function, m is an integer from 1 to 10, $A_i$ represents an organic radical, wherein the oligosidyl moiety of formula (VI) comprises a terminal cyclic hemiacetal residue in which the hemiacetalic hydroxy is replaced by the N of formula (VI), thereby to render said hemiacetal non-reducing.

17. Products of a general formula (VII)

oligosidyl-NH—CH—CO—[NH—(A$_i$)—CO]$_{\overline{m}}$—R
         |
         (CH$_2$)$_p$
         |
         CO$_2$H in which:

P=2 to 4,

R represents a group possessing an alcohol, phenol, thiol, or amine function, m is an integer from 1 to 10, $A_i$ represents an organic radical, wherein the oligosidyl moiety of formula (VII) comprises a terminal cyclic hemiacetal residue in which the hemiacetalic hydroxy is replaced by the N of formula (VII) thereby to render said hemiacetal non-reducing.

\* \* \* \* \*